(12) United States Patent
Takasaki et al.

(10) Patent No.: US 7,405,051 B2
(45) Date of Patent: Jul. 29, 2008

(54) METHOD OF SCREENING ANTIPLATELET AGENTS

(75) Inventors: Jun Takasaki, Ibaraki (JP); Mitsuyuki Matsumoto, Ibaraki (JP); Masazumi Kamohara, Ibaraki (JP); Tetsu Saito, Ibaraki (JP); Takahide Ohishi, Ibaraki (JP); Takatoshi Soga, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 689 days.

(21) Appl. No.: 10/333,844

(22) PCT Filed: Oct. 31, 2001

(86) PCT No.: PCT/JP01/09534

§ 371 (c)(1),
(2), (4) Date: Jan. 24, 2003

(87) PCT Pub. No.: WO02/36631

PCT Pub. Date: May 10, 2002

(65) Prior Publication Data

US 2003/0124626 A1    Jul. 3, 2003

(30) Foreign Application Priority Data

Nov. 1, 2000  (JP) .............................. 2000-334721
Jan. 11, 2001  (JP) .............................. 2001-003577

(51) Int. Cl.
| | |
|---|---|
| G01N 33/53 | (2006.01) |
| G01N 33/567 | (2006.01) |
| G01N 33/566 | (2006.01) |
| C12Q 1/68 | (2006.01) |
| C12N 5/00 | (2006.01) |
| C12N 5/06 | (2006.01) |
| C07K 1/00 | (2006.01) |

(52) U.S. Cl. ........................... 435/7.2; 435/7.21; 435/6; 435/325; 435/361; 530/350; 436/501; 436/503

(58) Field of Classification Search ........................ None
See application file for complete search history.

(56) References Cited

U.S. PATENT DOCUMENTS 6,762,029 B2 * 7/2004 Conley et al. ................. 435/7.1
2001/0046497 A1 * 11/2001 Zhang et al. ............. 424/143.1

FOREIGN PATENT DOCUMENTS

| WO | WO 98/50549 A2 | 11/1998 |
|---|---|---|
| WO | WO 9850549 | * 11/1998 |
| WO | WO 00/1/12704 | * 3/2000 |
| WO | WO 00/22131 A2 | 4/2000 |
| WO | WO 00/28028 A1 | 5/2000 |
| WO | WO 00/31258 A2 | 6/2000 |
| WO | WO 00/34333 A1 | 6/2000 |
| WO | WO 00/53742 A2 | 9/2000 |
| WO | WO 00/53742 A3 | 9/2000 |
| WO | WO 01/46454 A1 | 6/2001 |
| WO | WO 01/85791 A1 | 11/2001 |

OTHER PUBLICATIONS

Kunapuli S. 1998. TIPS 19:391-394.*
Jin, J. et al., "Molecular Basis for ADP-induced Platelet Activation" *J. Biol. Chem.* 273:2030-34 (1998).
Supplemental European Search Report dated Dec. 6, 2004.
Conley et al., Nov. 16, 2000, "Molecular Identification of the Platelet ADP Receptor Targeted by Antithrombotic Drugs," Blood, 96(11): 222a, Abstract #949; and BIOSIS No. 200100322024.
Zhang et al., Mar. 16, 2001, "ADP Is the Cognate Ligand for the Orphan G Protein-coupled Receptor SP1999," J. Biological Chemistry, 276(11): 8606-8615 (published, JBC Papers in Press, Dec. 4, 2000).
Jantzen et al., Jan. 1999, "Evidence for Two Distinct G-protein-coupled ADP Receptors Mediating Platelet Activation," Thrombosis and Haemostasis, 81(1): 111-117; and BIOSIS No. 199900164817.
Kunapuli, Nov. 1998, "Molecular Physiology of Platelet ADP Receptors," Drug Development Research, 45(3-4): 135-139; and BIOSIS No. 199900183703.
Puri et al., Jul. 1998, "Purinergic Receptors in Human Blood Platelets: Chemical Modification and Cloning Investigations," J. Protein Chemistry, 17(5): 429-451; and BIOSIS No. 199800400876.
von Kügelgen et al., Sep. 5, 2000, "Molecular pharmacology of P2Y-receptors," Naunyn-Schmiedeberg's Archives of Pharmacology, 362(4-5): 310-323; and BIOSIS No. 200100028429.

* cited by examiner

*Primary Examiner*—Lorraine Spector
*Assistant Examiner*—Shulamith H Shafer
(74) *Attorney, Agent, or Firm*—Finnegan, Henderson, Farabow, Garrett & Dunner, L.L.P.

(57) ABSTRACT

A screening tool for an antiplatelet agent wherein the tool is a human ADP receptor $P2T_{AC}$ protein, a variation functionally equivalent thereto, or a homologous protein thereof, and a screening tool for an antiplatelet agent wherein the tool is a transformant which is transformed with an expression vector comprising a DNA encoding the protein and is expressing the polypeptide are disclosed. Further, a method for detecting an ADP receptor $P2T_{AC}$ ligand, antagonist, or agonist by using the screening tool for an antiplatelet agent, and a method for screening an antiplatelet agent by the detecting method are disclosed.

2 Claims, 1 Drawing Sheet

Concentration of 2MeSAMP (μmol/L)

Concentration of AR-C69931MX (μmol/L)

METHOD OF SCREENING ANTIPLATELET AGENTS

TECHNICAL FIELD

The present invention relates to a method for screening antiplatelet agents.

BACKGROUND ART

The platelet was discovered in 1842 by Donne [C. R. Acad. Sci.(paris), 14, 336-368, 1842], and has long been regarded as a component of blood necessary for hemostasis. It is now known that the platelet plays not only a main role in the hemostatic system, but also multifunctional roles, for example, a clinically notable generation of arteriosclerosis, circulatory diseases including thrombotic diseases, metastasis of cancer, inflammation, rejection after grafting, participation in immune reaction, or the like.

At present, revascularization by pharmacological or physical methods is carried out to treat thrombotic diseases and ischemic diseases. However, it has been recently found that the activation, adhesion, and/or aggregation of the platelets is promoted by a collapse of blood vessel tissue including an endothelial cell after revascularization, or a collapse of a fibrinolysis-coagulation balance caused by a medicament per se, which becomes a clinical problem. For example, it is known that, after revascularization by a thrombolytic therapy using t-PA or the like, the fibrinolytic activity and/or coagulative activity are activated, and then the systemic fibrinolysis-coagulation balance collapses. Clinically, this causes re-occlusion, and becomes a critical problem therapeutically (J. Am. Coll. Cardiol. 12, 616-623, 1988).

In addition, the PTCA (Percutaneous transluminal coronary angioplasty) therapy has quickly become widely used, and has achieved good results in the treatment of diseases based on aortostenosis or coronary stenosis such as angina, myocardial infarction, or the like. However, the therapy injures blood vessel tissue including an endothelial cell, and acute coronary obstruction, and restenosis, which is observed in approximately 30% of cases, become a problem.

The platelet plays an important role in these various thrombotic disorders (such as re-occlusion or the like) after the revascularization therapy. Therefore, an antiplatelet agent is desired as an agent for treating or preventing these thrombotic disorders.

In this connection, adenosine 5'-diphosphate (ADP) is known as an important factor which induces or promotes the activation, adhesion, and aggregation of the platelets. ADP is released from platelets activated by collagen, thrombin, or the like, or from hemocytes, vascular endothelial cells, or organs injured by revascularization or the like. It is considered that ADP activates the platelets via a G protein-coupled ADP receptor P2T located in the platelet membrane (Biochem. J., 336, 513-523, 1998).

It has been suggested that a platelet ADP receptor $P2T_{PLC}$ which is coupled to Gq, one of the G proteins, and increases an intracellular $Ca^{2+}$ concentration via phospholipase C (PLC), and a platelet ADP receptor $P2T_{AC}$ which is coupled to Gi, one of the G proteins, and suppresses an activity of adenylate cyclase (AC) are present as platelet ADP receptors. At present, the platelet ADP receptor $P2T_{PLC}$ has been identified as the receptor known as platelet ADP receptor P2Y1, but the entity of platelet ADP receptor $P2T_{AC}$ is not identified (Kunapuli, S. P. et al., Trends Pharmacol. Sci., 19, 391-394, 1998).

It is considered that Ticlopidine or Clopidogrel used as an antiplatelet agent functions by inhibiting the ADP receptor $P2T_{AC}$ via its metabolite in a body (Savi, P. J., Pharmaclo. Exp. Ther., 269, 772-777, 1994). Further, ARL67085, which is synthesized as a derivative of adenosine triphosphate (ATP), which is an ADP receptor antagonist in a body, exhibits an activity of suppressing a platelet aggregation by the antagonist activity against the platelet ADP receptor $P2T_{AC}$, and the effectiveness thereof is proven by using a thrombosis model (Mills, D. C., Thromb. Hemost., 76, 835-856, 1996; and Humphries, R. G., Trends Pharmacol. Sci., 16, 179-181, 1995). Further, a derivative of Ap4A [$P^1,P^4$-di(adenosine-5') tetraphosphate] exhibits an activity suppressing the platelet aggregation by ADP, by the antagonist activity against the platelet ADP receptor $P2T_{AC}$, and the effectiveness thereof is proven by using a thrombosis model (Kim, B. K., Proc. Natl. Acad. Sci. USA, 89, 2370-2373, 1992).

From the above information, an antagonist against the platelet ADP receptor $P2T_{AC}$ is desired as a strong antiplatelet agent. However, Ticlopidine or Clopidogrel exhibits a weak antiplatelet activity, and has problems such as a strong side effect or the like. Further, ARL67085 or derivatives thereof (ATP analogues), derivatives of Ap4A, or the like, which is studied as the ADP receptor antagonist, is a derivative of nucleotide, and then an oral bioavailability is not sufficient, and further problems arise such as a weak activity of suppressing the platelet aggregation. Therefore, an ADP receptor antagonist having a strong oral bioavailability is intensely desired (CAPRIE STEERING COMMITTEE, Lancet, 348, 1329-1339, 1996).

However, the ADP receptor $P2T_{AC}$ protein has not been identified as yet. Therefore, it is difficult to construct a convenient system for screening such a compound, and farther, the development of the ADP receptor $P2T_{AC}$ antagonist has not progressed.

In this connection, with regard to a DNA encoding a polypeptide consisting of the same amino acid sequence as that of a human ADP receptor $P2T_{AC}$ protein, which may be used in the present invention, and an amino acid sequence deduced from the DNA, there are several reports (WO00/22131, WO00/31258, WO00/28028, and WO98/50549 pamphlets). However, ligands are not elucidated in the reports, and no reports disclose that the protein is an ADP receptor located in the platelet.

DISCLOSURE OF INVENTION

Therefore, the object of the present invention is to provide a convenient screening system to obtain an adenosine diphosphate (ADP) receptor $P2T_{AC}$ antagonist which is useful as an antiplatelet agent, and a novel antiplatelet agent.

With the aim of solving the aforementioned problems, the present inventors have conducted intensive studies and, as a result, successfully isolated a nucleic acid (more particularly, an HORK3 gene) encoding the $P2T_{AC}$ receptor, and have determined the nucleotide sequence thereof and the deduced amino acid sequence. Further, the inventors prepared a vector comprising the nucleic acid encoding the receptor, and a host cell comprising the vector, and made it possible to produce a novel recombinant $P2T_{AC}$ receptor by expressing the $P2T_{AC}$ receptor by the use of the host cell. The inventors confirmed that the receptor exhibited an ADP receptor $P2T_{AC}$ activity, and thus the receptor and the cell expressing the receptor could be used as a screening tool for an antiplatelet agent. The inventors established a method for detecting whether or not a test compound is an ADP receptor $P2T_{AC}$ ligand, antagonist, or agonist by using the receptor or the cell expressing the receptor, and a method for screening an antiplatelet agent by using the detecting method. The inventors confirmed that compounds known to exhibit an antiplatelet activity (more particularly 2MeSAMP or AR-C69931MX) exhibited an antagonist activity of the receptor, by using the detecting method, and showed that an antagonist of the receptor was certainly useful as an antiplatelet agent. Further, the inventors established a process for manufacturing a pharmaceutical composition for antiplatelet, comprising the detecting step, and completed the present invention.

Namely, the present invention relates to:

[1] a screening tool for an antiplatelet agent, wherein the tool is
(1) a polypeptide (hereinafter sometimes referred to as "human ADP receptor $P2T_{AC}$ protein") having an amino acid sequence of SEQ ID NO: 2, or
(2) a polypeptide (hereinafter referred to as "variation functionally equivalent") having an amino acid sequence in which one or plural amino acids are deleted, substituted, and/or added at one or plural positions in an amino acid sequence of SEQ ID NO: 2, and exhibiting an activity (hereinafter referred to as "ADP receptor $P2T_{AC}$ activity") of suppressing an adenylate cyclase activity by binding to ADP and coupling with Gi:

[2] a screening tool for an antiplatelet agent, wherein the tool is a polypeptide (hereinafter referred to as "homologous protein") having an amino acid sequence having a 90% or more homology with an amino acid sequence of SEQ ID NO: 2, and exhibiting an activity of suppressing an adenylate cyclase activity by binding to ADP and coupling with Gi (hereinafter the screening tools of the items [1] and [2] for an antiplatelet agent are collectively referred to as "polypeptide-type screening tool for an antiplatelet agent");

[3] a screening tool for an antiplatelet agent, wherein the tool is a transformant which is transformed with an expression vector comprising a DNA encoding (1) a polypeptide having an amino acid sequence of SEQ ID NO: 2 (i.e., human ADP receptor $P2T_{AC}$ protein) or (2) a polypeptide having an amino acid sequence in which one or plural amino acids are deleted, substituted, and/or added at one or plural positions in an amino acid sequence of SEQ ID NO: 2, and exhibiting an activity of suppressing an adenylate cyclase activity by binding to ADP and coupling with Gi (i.e., variation functionally equivalent), and is expressing the polypeptide;

[4] a screening tool for an antiplatelet agent, wherein the tool is a transformant which is transformed with an expression vector comprising a DNA encoding a polypeptide having an amino acid sequence having a 90% or more homology with an amino acid sequence of SEQ ID NO: 2, and exhibiting an activity of suppressing an adenylate cyclase activity by binding to ADP and coupling with Gi (i.e., homologous protein), and is expressing the polypeptide (hereinafter the screening tools of the items [3] and [4] for an antiplatelet agent are collectively referred to as "transformant-type screening tool for an antiplatelet agent");

[5] a method for detecting whether or not a compound to be tested is an ADP receptor $P2T_{AC}$ ligand, comprising the steps of:
bringing a polypeptide of the item [1] or [2] (i.e., the human ADP receptor $P2T_{AC}$ protein, variation functionally equivalent, or homologous protein), a cell membrane fraction comprising the polypeptide, or a transformant of the item [3] or [4] into contact with the compound to be tested, in the presence of a labeled ligand of an ADP receptor $P2T_{AC}$, and analyzing a change of an amount of the labeled ligand which binds to the polypeptide, the cell membrane fraction, or the transformant (hereinafter referred to as "ligand detecting method");

[6] a method for detecting whether or not a compound to be tested is an ADP receptor $P2T_{AC}$ antagonist or agonist, comprising the steps of:
bringing the compound to be tested into contact with a transformant of the item [3] or [4] which is co-expressing a G protein chimera comprising a polypeptide fragment having an activity promoting a phospholipase C activity of a G protein promoting the phospholipase C activity and a polypeptide fragment having a receptor-coupled activity of Gi, said G protein chimera having an amino acid sequence of SEQ ID NO: 11 at the C-terminus; and
analyzing a change of an intracellular $Ca^{2+}$ concentration in the transformant (hereinafter referred to as "$Ca^{2+}$-type detecting method");

[7] a method for detecting whether or not a compound to be tested is an ADP receptor $P2T_{AC}$ antagonist or agonist, comprising the steps of:
bringing a transformant of the item [3] or [4] into contact with the compound to be tested, in the presence of a platelet ADP receptor $P2T_{AC}$ agonist, and
analyzing a change of an intracellular cAMP concentration in the transformant (hereinafter referred to as "cAMP-type detecting method");

[8] a method for screening an antiplatelet agent, comprising the steps of:
detecting whether or not a compound to be tested is an ADP receptor $P2T_{AC}$ ligand, antagonist, or agonist by the ligand detecting method, the $Ca^{2+}$-type detecting method, or the cAMP-type detecting method, or a combination thereof, and selecting the ADP receptor $P2T_{AC}$ antagonist; and

[9] a process for manufacturing a pharmaceutical composition for antiplatelet, comprising the steps of:
detecting whether or not a compound to be tested is an ADP receptor $P2T_{AC}$ ligand, antagonist, or agonist by the ligand detecting method, the $Ca^{2+}$-type detecting method, or the cAMP-type detecting method, or a combination thereof, and preparing a medicament.

The "Gi" is a subfamily of the G proteins which are coupled to a receptor and function as a signal transduction and amplification factor into a cell, and a G protein which suppresses an adenylate cyclase activity. When the adenylate cyclase activity is suppressed, for example, an intracellular cAMP concentration decreases.

The "G protein promoting the phospholipase C activity" is a subfamily of G proteins which are coupled to a receptor and function as a signal transduction and amplification factor into a cell, and a G protein which promotes a phospholipase C activity. When the phospholipase C activity is induced, for example, an intracellular $Ca^{2+}$ concentration increases. As the G protein promoting the phospholipase C activity, there may be mentioned, for example, Gq.

The "ADP receptor $P2T_{AC}$" means a polypeptide having the ADP receptor $P2T_{AC}$.

BEST MODE FOR CARRYING OUT THE INVENTION

Figure 1:
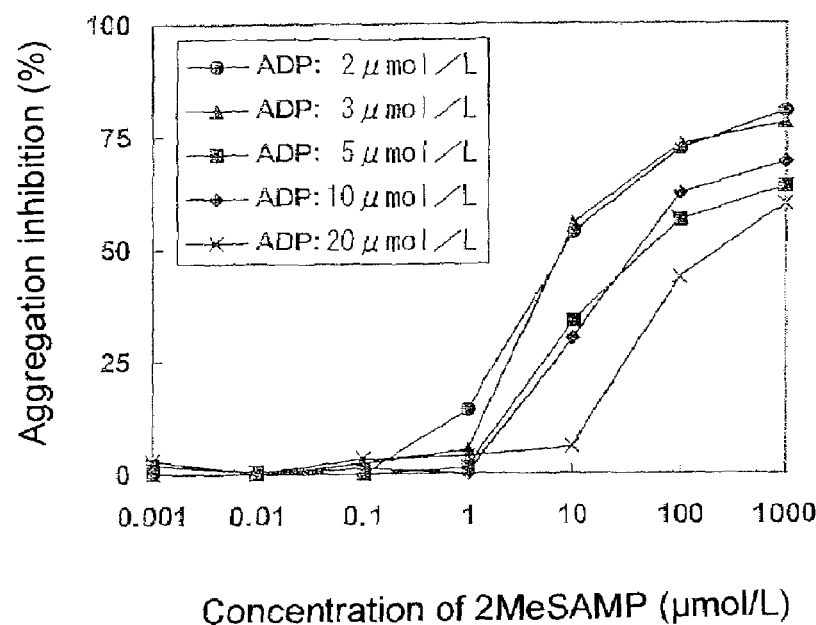
FIG. 1 is a graph showing the effect of 2MeSAMP in an ADP-induced platelet aggregation of platelet-rich plasma (PRP) derived from human blood-treated with sodium citrate.

The present invention will be explained in detail hereinafter.

(1) The Screening Tool for an Antiplatelet Agent

The screening tool of the present invention for an antiplatelet agent includes a polypeptide-type screening tool for an antiplatelet agent and a transformant-type screening tool for an antiplatelet agent.

1) The Polypeptide-type Screening Tool for an Antiplatelet Agent

The polypeptide-type screening tool of the present invention for an antiplatelet agent includes
(i) a screening tool for an antiplatelet agent, wherein the tool is the human ADP receptor $P2T_{AC}$ protein, i.e., the polypeptide having the amino acid sequence of SEQ ID NO: 2;
(ii) a screening tool for an antiplatelet agent, wherein the tool is a variation functionally equivalent, i.e., a polypeptide having an amino acid sequence in which one or plural amino acids are deleted, substituted, and/or added at one or plural positions in the amino acid sequence of SEQ ID NO: 2, and exhibiting the ADP receptor $P2T_{AC}$ activity; and
(iii) a screening tool for an antiplatelet agent, wherein the tool is a homologous protein, i.e., a polypeptide having an amino acid sequence having a 90% or more homology with the amino acid sequence of SEQ ID NO: 2, and exhibiting the ADP receptor $P2T_{AC}$ activity.

The polypeptide having the amino acid sequence of SEQ ID NO: 2, which may be used as the polypeptide-type screening tool of the present invention for an antiplatelet agent, is a human ADP receptor $P2T_{AC}$ protein consisting of 342 amino acid residues. Although it has been suggested that the ADP receptor $P2T_{AC}$ protein exists in platelets, the entity thereof had not been identified until the present inventors first elucidated its function.

Then, it was first published in a reference after the priority date of the present application that the polypeptide having the amino acid sequence of SEQ ID NO: 2 is a platelet ADP receptor [Nature, 409, Jan. 11, 2001, 202-207; J. B. C., 276, (11), March 16, 8608-8615, 2001; WO01/46454 pamphlet]. In the basic patent application of the priority of the WO01/46454 pamphlet, although a rat ADP receptor gene was cloned and the sequence thereof was determined, as to a human ADP receptor gene, only a clone containing a partial sequence was obtained and the sequence thereof was determined. Therefore, it was first accomplished by the present applicant that the human ADP receptor $P2T_{AC}$ protein and the polynucleotide encoding the protein was obtained, the function thereof was elucidated, and a patent application relating to the invention of the method for screening an antiplatelet agent using them was filed.

The variation functionally equivalent which may be used as the polypeptide-type screening tool of the present invention for an antiplatelet agent is not particularly limited, so long as it is a polypeptide having an amino acid sequence in which one or plural (preferably 1 to 10, more preferably 1 to 5) amino acids are deleted, substituted, and/or added at one or plural positions in the amino acid sequence of SEQ ID NO: 2, and exhibiting the ADP receptor $P2T_{AC}$ activity. Further, an origin of the variation functionally equivalent is not limited to a human.

The variation functionally equivalent includes, for example, human variations of the human ADP receptor $P2T_{AC}$, and ADP receptors $P2T_{AC}$ derived from organisms other than a human (such as a mouse, a rat, a hamster, or a dog) or variations thereof, and further proteins obtained by artificially modifying these native proteins (i.e., human variations, or ADP receptors $P2T_{AC}$ derived from organisms other than a human or variations thereof) or the human ADP receptor $P2T_{AC}$ by genetic engineering techniques. The term "variation" as used herein means an individual difference between the same proteins in the same species or a difference between homologous proteins in several species.

Human variations of the human ADP receptor $P2T_{AC}$, or ADP receptors $P2T_{AC}$ derived from organisms other than a human or variations thereof may be obtained by those skilled in the art based on the information of a nucleotide sequence (for example, the nucleotide sequence of SEQ ID NO: 1) of the human ADP receptor $P2T_{AC}$ gene. In this connection, genetic engineering techniques may be performed in accordance with known methods (for example, Maniatis, T. et al., "Molecular Cloning—A Laboratory Manual", Cold Spring Harbor Laboratory, NY, 1982, or the like), unless otherwise specified.

For example, an appropriate probe or appropriate primers are designed in accordance with the information of a base sequence of the human ADP receptor $P2T_{AC}$ gene. A PCR method or a hybridization method is carried out using a sample (for example, total RNA or an mRNA fraction, a cDNA library, or a phage library) derived from an organism (for example, a mammal such as a human, a mouse, a rat, a hamster, or a dog) of interest and the primers or the probe to obtain a gene encoding the protein. A desired protein can be obtained by expressing the resulting gene in an appropriate expression system and confirming that the expressed protein suppresses the adenylate cyclase activity by binding to ADP and coupling with Gi, for example, by the method described in Example 3 or 4.

Further, the protein artificially modified by genetic engineering techniques can be obtained by, for example, the following procedure. A gene encoding the protein is obtained by a conventional method such as site-specific mutagenesis (Mark, D. F. et al., Proc. Natl. Acad. Sci. USA, 81, 5662-5666, 1984). A desired protein can be obtained by expressing the resulting gene in an appropriate expression system and confirming that the expressed protein suppresses the adenylate cyclase activity by binding to ADP and coupling with Gi, for example, by the method described in Example 3 or 4.

The homologous protein which may be used as the polypeptide-type screening tool of the present invention for an antiplatelet agent is not particularly limited, so long as it is a polypeptide having an amino acid sequence having a 90% or more homology with the amino acid sequence of SEQ ID NO: 2, and exhibiting the ADP receptor $P2T_{AC}$ activity. The homologous protein may have an amino acid sequence having preferably a 95% or more homology, more preferably a 98% or more homology, most preferably a 99% or more homology, with respect to the amino acid sequence of SEQ ID NO: 2.

The term "homology" as used herein means a value which can be obtained by a BLAST package [Basic local alignment search tool; Altschul, S. F. et al., J. Mol. Biol., 215, 403-410, (1990)]. The homology in the amino acid sequence can be calculated by a BLAST search algorithm. More particularly, this value can be obtained by using a bl2seq program (Tatiana A. Tatusova and Thomas L. Madden, FEMS Microbiol. Lett., 174, 247-250, 1999) with a default parameter in a BLAST package (sgi32bit edition, version 2.0.12; obtained from NCBI). Default parameters of the bl2seq program include "blastp" as a search program, "0" as a cost to open a gap, "0"

as a cost to extend a gap, "SEG" as a filter of the query sequence, and "BLOSUM62" as a matrix.

The polypeptides which may be used as the polypeptide-type screening tool of the present invention for an antiplatelet agent (i.e., the human ADP receptor P2T$_{AC}$ protein, the variations functionally equivalent, and the homologous proteins; hereinafter referred to as "polypeptide for a screening tool") may be obtained by various known methods, such as known genetic engineering techniques using a gene encoding a protein of interest. More particularly, the polypeptide for a screening tool may be prepared by culturing a transformant described below (i.e., a transformant which is transformed with an expression vector comprising a DNA encoding the polypeptide for a screening tool and expressing the polypeptide) under a condition in which an expression of the polypeptide for a screening tool may be performed, and separating and purifying the protein of interest from the resulting culture by commonly used methods for a separation and a purification of receptor proteins.

When the polypeptide for a screening tool is prepared, the method for obtaining the gene encoding the polypeptide is not particularly limited. For example, when the human ADP receptor P2T$_{AC}$ protein is prepared, for example, the DNA consisting of the nucleotide sequence of SEQ ID NO: 1 may be used as the gene encoding the protein. In this connection, codons for each amino acid are known and can be optionally selected and determined by the conventional method, for example, by taking a codon usage of each host to be used into consideration (Crantham, R. et al., Nucleic Acids Res., 9, r43-r74, 1981).

The DNA consisting of the nucleotide sequence of SEQ ID NO: 1 may be obtained by, for example, ligating DNA fragments prepared by a chemical synthesis method, or a polymerase chain reaction (PCR) method (Saiki, R. K. et al., Science, 239, 487-491, 1988) using a cDNA library derived from a cell or tissue capable of producing the human ADP receptor P2T$_{AC}$ protein as a template and an appropriate primer set designed in accordance with the nucleotide sequence of SEQ ID NO: 1. As the cell or tissue capable of producing the human ADP receptor P2T$_{AC}$ protein, there may be mentioned, for example, human platelets, the human brain, or the like. As the primer set, there may be mentioned, for example, a combination of an oligonucleotide consisting of the nucleotide sequence of SEQ ID NO: 3 and an oligonucleotide consisting of the nucleotide sequence of SEQ ID NO: 4.

A separation and purification method which may be used for preparing the polypeptide for a screening tool is not particularly limited, but can be performed, for example, in accordance with the following procedure. For example, a cell membrane fraction containing the polypeptide for a screening tool can be obtained by culturing cells expressing the polypeptide for a screening tool on the surface thereof, suspending the cultured cells in a buffer, homogenizing the suspension, and centrifuging the homogenate. After the resulting cell membrane fraction is solubilized, the polypeptide for a screening tool can be purified by treating the mixture with a commonly used treatment with a protein precipitant, ultrafiltration, various liquid chromatography techniques such as molecular sieve chromatography (gel filtration), adsorption chromatography, ion exchange chromatography, affinity chromatography, or high performance liquid chromatography (HPLC), or dialysis, or a combination thereof. In this connection, when the cell membrane fraction is solubilized, characteristics of the receptor can be maintained after the solubilization, by using as mild as possible a solubilizing agent (such as CHAPS, Triton X-100, digitonin or the like).

When the polypeptide for a screening tool is prepared, a confirmation of the expression of the polypeptide, a confirmation of intracellular localization thereof, a purification thereof, or the like may be easily carried out by expressing the polypeptide for a screening tool as a fusion protein with an appropriate marker sequence in frame, if necessary. As the marker sequence, there may be mentioned, for example, a FLAG epitope, a hexa-histidine tag, a hemagglutinin tag, a myc epitope, or the like. Further, by inserting a specific sequence recognized by a protease such as enterokinase, factor Xa, thrombin, or the like between the marker sequence and the polypeptide for a screening tool, the marker sequence may be removed by the protease. For example, there is a report in which a muscarinic acetylcholine receptor and a hexa-histidine tag were connected by a thrombin recognition sequence (Hayashi, M. K. and Haga, T., J. Biochem., 120, 1232-1238, 1996).

2) The Transformant-type Screening Tool for an Antiplatelet Agent

The transformant-type screening tool of the present invention for an antiplatelet agent includes (i) a screening tool for an antiplatelet agent, wherein the tool is a transformant which is transformed with an expression vector comprising a DNA encoding the human ADP receptor P2T$_{AC}$ protein and is expressing the polypeptide;

(ii) a screening tool for an antiplatelet agent, wherein the tool is a transformant which is transformed with an expression vector comprising a DNA encoding the variation functionally equivalent and is expressing the polypeptide; and (iii) a screening tool for an antiplatelet agent, wherein the tool is a transformant which is transformed with an expression vector comprising a DNA encoding the homologous protein and is expressing the polypeptide.

A host cell which may be used for preparing the transformants (hereinafter referred to as "transformant for a screening tool") which may be used as the transformant-type screening tool of the present invention for an antiplatelet agent is not particularly limited, so long as the polypeptide for a screening tool can be expressed. As the host cell, there may be mentioned, for example, commonly used known microorganisms, such as Escherichia coli or Saccharomyces cerevisiae, or known cultured cells, such as vertebral cells (for example, a CHO cell, HEK293 cell, or COS cell) or insect cells (for example, an Sf9 cell). As the vertebral cell, there may be mentioned, for example, a COS cell as a simian cell (Gluzman, Y., Cell, 23, 175-182, 1981), a dihydrofolate reductase defective strain of a Chinese hamster ovary cell (CHO) (Urlaub, G. and Chasin, L. A., Proc. Natl. Acad. Sci. USA, 77, 4216-4220, 1980), a human embryonic kidney derived HEK293 cell, or a 293-EBNA cell (Invitrogen) obtained by introducing an EBNA-1 gene of Epstein Barr Virus into the HEK293 cell.

An expression vector which may be used for preparing the transformant for a screening tool is not particularly limited, so long as the polypeptide for a screening tool can be expressed. An appropriate expression vector can be selected in accordance with a host cell to be used.

As an expression vector for a vertebral cell, a vector containing a promoter positioned upstream of a gene to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854-864, 1981), pEF-BOS containing a human elongation factor promoter (Mizushima, S. and Nagata, S., Nucleic Acids Res., 18,5322, 1990), pCEP4 containing a cytomegalovirus promoter (Invitrogen), or the like.

More particularly, when the COS cell is used as the host cell, a vector having an SV40 replication origin, capable of performing an autonomous replication in the COS cell, and having a transcription promoter, a transcription termination signal, and an RNA splicing site, may be used as the expression vector. As the vector, there may be mentioned, for example, pME18S (Maruyama, K. and Takebe, Y., Med. Immunol., 20, 27-32, 1990), pEF-BOS (Mizushima, S. and Nagata, S., Nucleic Acids Res., 18, 5322, 1990), pCDM8 (Seed, B., Nature, 329, 840-842, 1987), or the like.

The expression vector may be incorporated into COS cells by, for example, a DEAE-dextran method (Luthman, H. and Magnusson, G., Nucleic Acids Res., 11, 1295-1308, 1983), a calcium phosphate-DNA co-precipitation method (Graham, F. L. and van der Ed, A. J., Virology, 52, 456-457, 1973), a method using a cationic liposome reagent (Lipofectamine; Gibco BRL), an electroporation method (Neumann, E. et al., EMBO J., 1, 841-845, 1982), or the like.

When the CHO cell is used as the host cell, a transformant capable of stably producing the polypeptide for a screening tool can be obtained by carrying out a co-transfection of an expression vector comprising the DNA encoding the polypeptide for a screening tool, together with a vector capable of expressing a neo gene which functions as a G418 resistance marker, such as pRSVneo (Sambrook, J. et al., "Molecular Cloning—A Laboratory Manual", Cold Spring Harbor Laboratory, NY, 1989), pSV2-neo (Southern, P. J. and Berg, P., J. Mol. Appl. Genet., 1, 327-341,1982), or the like, and selecting a G418 resistant colony.

When the 293-EBNA cell is used as the host cell, for example, pCEP4 (Invitrogen) containing a replication origin of Epstein Barr Virus and capable of performing an autonomous replication in the 293-EBNA cell, or the like may be used as the expression vector.

The transformant for a screening tool may be cultured in accordance with a conventional method, and the polypeptide for a screening tool is produced in the cell or on the cell surface. As a medium to be used in the culturing, a medium commonly used in a selected host cell may be appropriately selected. For example, in the case of the COS cell, for example, a medium such as an RPMI-1640 medium, a Dulbecco's modified Eagle's minimum essential medium (DMEM), or the like may be used, by supplementing it with a serum component such as fetal bovine serum (FBS) or the like if necessary. In the case of the 293-EBNA cell, a medium such as a Dulbecco's modified Eagle's minimum essential medium (DMEM) or the like with a serum component such as fetal bovine serum (FBS) or the like and G418 may be used.

The transformant for a screening tool is not particularly limited, so long as the polypeptide for a screening tool is expressed. As the transformant for a screening tool, it is preferable to express a G protein in which the amino acid sequence at the C-terminus is that of SEQ ID NO: 11 (Asp-Cys-Gly-Leu-Phe), in addition to the polypeptide for a screening tool. The amino acid sequence of SEQ ID NO: 11 is that consisting of five amino acid residues at the C-terminus of Gi. Hereinafter the "G protein in which the amino acid sequence at the C-terminus is that of SEQ ID NO: 11" will be referred to as "C-terminus Gi-type G protein".

As the C-terminus Gi-type G protein, there may be mentioned, for example, (1) Gi, or
(2) a G protein chimera which comprises a polypeptide fragment having the activity promoting a phospholipase C activity of a G protein (such as Gq) promoting the phospholipase C activity and a polypeptide fragment having a receptor-coupled activity of Gi, and which further has an amino acid sequence of SEQ ID NO: 11 at the C-terminus. Hereinafter, the G protein chimera comprising a polypeptide fragment having the activity of promoting a phospholipase C activity and a polypeptide fragment having a receptor-coupled activity of Gi will be referred to as Gqi.

The polypeptide for a screening tool recognizes the amino acid sequence consisting of five amino acid residues at the C-terminus of Gi (i.e., the amino acid sequence of SEQ ID NO: 11), and binds to Gi. Therefore, the polypeptide for a screening tool may be bound to not only Gi, but also Gqi. When the polypeptide for a screening tool and the C-terminus Gi-type G protein are expressed in the transformant for a screening tool, these polypeptides can bind to each other in the cell.

The "polypeptide fragment having the activity of promoting a phospholipase C activity of a Gq" is not particularly limited, so long as it does not comprise a C-terminal amino acid sequence which is necessary to bind to a Gq-coupled platelet ADP receptor $P2T_{PLC}$, and exhibits the activity of promoting the phospholipase C activity. There may be mentioned, for example, a polypeptide fragment at the N-terminal side of Gq in which the amino acid sequence consisting of five amino acid residues at the C-terminus is deleted.

The "polypeptide fragment having a receptor-coupled activity of Gi" is not particularly limited, so long as it comprises the amino acid sequence consisting of five amino acid residues at the C-terminus of Gi, and does not exhibit an activity suppressing the adenylate cyclase activity. There may be mentioned, for example, a polypeptide fragment at the C-terminal side of Gi, consisting of the amino acid sequence of SEQ ID NO: 11.

(2) The Detecting Method for an ADP Receptor $P2T_{AC}$ Ligand, Antagonist, or Agonist It can be detected whether or not a test compound is an ADP receptor $P2T_{AC}$ ligand, antagonist, or agonist, by using the polypeptide for a screening tool or the transformant for a screening tool as a detecting tool.

The method of the present invention for detecting whether or not a test compound is an ADP receptor $P2T_{AC}$ ligand, antagonist, or agonist includes 1) a method for detecting whether or not a test compound is a ligand against the platelet ADP receptor $P2T_{AC}$ (i.e., ligand detecting method);
2) a method for detecting whether or not a test compound is an antagonist or agonist against the platelet ADP receptor $P2T_{AC}$, by the use of changes of an intracellular $Ca^{2+}$ concentration in the transformant as an indicator (i.e., $Ca^{2+}$-type detecting method);
3) a method for detecting whether or not a test compound is an antagonist or agonist against the platelet ADP receptor $P2T_{AC}$, by the use of changes of an intracellular cAMP content in the transformant as an indicator (i.e., cAMP-type detecting method); and
4) a method for detecting whether or not a test compound is an antagonist or agonist against the platelet ADP receptor $P2T_{AC}$, by the use of a GTPγS binding method (i.e., GTPγS binding-type detecting method).

These detecting methods will be explained in this order hereinafter.

1) The Ligand Detecting Method

The ligand detecting method of the present invention is not particularly limited, so long as (i) the human ADP receptor $P2T_{AC}$ protein, variation functionally equivalent, or homologous protein (hereinafter referred to as "polypeptide for a detecting tool"), a cell membrane fraction comprising the polypeptide for a detecting tool, or a transformant expressing the polypeptide for a detecting tool (hereinafter the polypeptide for a detecting tool, the cell membrane fraction, and the transformant are collectively referred to as "ligand-detecting tool") and (ii) a labeled ligand are used. It may be carried out, for example, in accordance with the following procedure.

The ligand-detecting tool is prepared. Assay conditions (for example, a buffer to be used and the concentration thereof, ions to be added to the buffer and the concentration thereof, and the pH in the assay system) are optimized. The ligand-detecting tool and a labeled ligand are incubated in the optimized buffer, together with a test compound, for a predetermined time. As the labeled ligand, for example, [$^3$H] 2-methylthio-ADP (2MeSADP) may be used. After the reaction, the whole is filtered with a glass filter or the like, and the filter is washed with an appropriate volume of the buffer. The remaining radioactivity on the filter is measured by a liquid scintillation counter or the like. It may be detected whether or not the test compound is a ligand against the ADP receptor $P2T_{AC}$, by the obtained binding inhibition of the radioactive ligand as an indicator. More particularly, when the remaining radioactivity on the filter in the presence of the test compound is lower than that in the absence of the test compound, it may be decided that the test compound is a ligand against the ADP receptor $P2T_{AC}$. It may be carried out, for example, under the conditions described in Example 6.

2) The $Ca^{2+}$-type Detecting Method

In the $Ca^{2+}$-type detecting method of the present invention, a transformant (hereinafter referred to as transformant for $Ca^{2+}$-type detection) co-expressing (i) the polypeptide for a detecting tool and (ii) a G protein chimera (such as Gqi) which comprises a polypeptide fragment having the activity promoting a phospholipase C activity of a G protein promoting the phospholipase C activity and a polypeptide fragment having a receptor-coupled activity of Gi, and which further has an amino acid sequence of SEQ ID NO: 11 at the C-terminus is used as the transformant. As to the transformant, it is preferable to use a cell in which an intracellular $Ca^{2+}$ concentration is not increased by ADP, as a host cell before the transformation. As the host cell, there may be mentioned, for example, C6-15, one of rat glioma cell lines (Change, K. et al., J. Biol. Chem., 270, 26152-26158, 1995).

In the case of detecting whether or not a test compound is an agonist in the $Ca^{2+}$-type detecting method of the present invention, the transformant for $Ca^{2+}$-type detection is brought into contact with a test compound, and then changes of the intracellular $Ca^{2+}$ concentration in the transformant for $Ca^{2+}$-type detection are analyzed (i.e., measured or detected) directly or indirectly. Changes of the $Ca^{2+}$ concentration may be, for example, directly analyzed by the use of a calcium-binding fluorescence reagent (such as fura2, fluo3, or the like), or indirectly analyzed by analyzing a transcriptional activity of a gene [such as a gene obtained by introducing an activator protein 1 (AP1) responsive sequence upstream of a luciferase gene] in which a regulation of the transcription is dependent on the $Ca^{2+}$ concentration.

When the transformant for $Ca^{2+}$-type detection is brought into contact with a test compound, and then the intracellular $Ca^{2+}$ concentration therein increases, it may be decided that the test compound is an agonist against the ADP receptor $P2T_{AC}$. In this connection, as a control, a similar procedure is carried out using a control transformant not expressing the polypeptide for a detecting tool but expressing Gqi, or a host cell before the transformation, instead of the transformant for $Ca^{2+}$-type detection co-expressing the polypeptide for a detecting tool and Gqi, and then it is preferable to confirm that the intracellular $Ca^{2+}$ concentration in the control transformant or host cell is not increased by the test compound.

In the case of detecting whether or not a test compound is an antagonist in the $Ca^{2+}$-type detecting method of the present invention, the transformant for $Ca^{2+}$-type detection is brought into contact with a test compound in the presence of a platelet ADP receptor $P2T_{AC}$ agonist (such as 2MeSADP or ADP), and then changes of the intracellular $Ca^{2+}$ concentration therein are analyzed (i.e., measured or detected) directly or indirectly. When the transformant for $Ca^{2+}$-type detection is brought into contact with a test compound in the presence of a platelet ADP receptor $P2T_{AC}$ agonist, and then the increase in the intracellular $Ca^{2+}$ concentration therein by the agonist is inhibited or suppressed by the test compound, it may be decided that the test compound is an antagonist against the ADP receptor $P2T_{AC}$. This may be carried out, for example, under the conditions described in Example 3.

In this connection, as a control, the transformant for $Ca^{2+}$ detection is brought into contact with the platelet ADP receptor $P2T_{AC}$ agonist in the absence of a test compound, and then it is necessary to confirm a degree of the increase in the intracellular $Ca^{2+}$ concentration therein by the agonist.

As described above, in the $Ca^{2+}$-type detecting method of the present invention, Gi per se is not used as the coupled protein, but Gqi is used. Therefore, it is possible to detect whether or not a test compound is an antagonist or agonist by analyzing the $Ca^{2+}$ concentration, not the cAMP concentration. In general, measurement can be carried out more easily and rapidly by using the $Ca^{2+}$ concentration, in comparison with the cAMP concentration.

3) The cAMP-type Detecting Method

In the cAMP-type detecting method of the present invention, a transformant expressing the polypeptide for a detecting tool (hereinafter referred to as "transformant for cAMP-type detection") is used as the transformant. Gi is constitutively expressed in a commonly used host cell, and thus the transformant for cAMP-type detection may be obtained by transforming a host cell with an expression vector comprising a DNA encoding the polypeptide for a detecting tool. As to the transformant, it is preferable to use a cell in which an intracellular cAMP concentration is not decreased by ADP, as a host cell before the transformation. As the host cell, there may be mentioned, for example, a CHO cell.

In the case of detecting whether or not a test compound is an agonist in the cAMP-type detecting method of the present invention, the transformant for cAMP-type detection is brought into contact with a test compound, and then changes of the intracellular cAMP concentration in the transformant for cAMP-type detection are analyzed (i.e., measured or detected) directly or indirectly. It is preferable that the transformant for cAMP-type detection is brought into contact with a test compound in the presence of a compound (such as forskolin) capable of increasing the cAMP concentration.

Changes of the cAMP concentration may be, for example, directly analyzed by the use of a commercially available cAMP measuring kit (Amersham or the like), or indirectly analyzed by analyzing a transcriptional activity of a gene [such as a gene obtained by introducing a cAMP responsive element (CRE) upstream of a luciferase gene] in which a regulation of the transcription is dependent on the cAMP concentration.

When the transformant for cAMP-type detection is brought into contact with a test compound, and then the intracellular cAMP concentration therein decreases, it may be decided that the test compound is an agonist against the ADP receptor P2T$_{AC}$. In this case, the decrease in the cAMP concentration by a test compound may be easily decided, when a compound (such as forskolin) capable of increasing the cAMP concentration coexists. In this connection, as a control, a similar procedure is carried out using a host cell not expressing the polypeptide for a detecting tool, instead of the transformant for cAMP-type detection expressing the polypeptide for a detecting tool and Gi, and then it is preferable to confirm that the intracellular cAMP concentration in the host cell is not decreased by the test compound.

In the case of detecting whether or not a test compound is an antagonist in the cAMP-type detecting method of the present invention, the transformant for cAMP-type detection is brought into contact with a test compound in the presence of a platelet ADP receptor P2T$_{AC}$ agonist (such as 2MeSADP or ADP), and then changes of the intracellular cAMP concentration therein are analyzed (i.e., measured or detected) directly or indirectly. When the transformant for cAMP-type detection is brought into contact with a test compound in the presence of a platelet ADP receptor P2T$_{AC}$ agonist (such as 2MeSADP or ADP), and then the decrease in the intracellular cAMP concentration therein by the agonist is inhibited or suppressed by the test compound, it may be decided that the test compound is an antagonist against the ADP receptor P2T$_{AC}$. In this case, the change of the cAMP concentration by a test compound may be easily decided, when a compound (such as forskolin) capable of increasing the cAMP concentration coexists. It may be carried out, for example, under the conditions described in Example 4 or 5.

Further, as a control, the transformant for cAMP detection is brought into contact with the platelet ADP receptor P2T$_{AC}$ agonist in the absence of a test compound, and then it is necessary to confirm a degree of the decrease in the intracellular cAMP concentration therein by the agonist.

4) The GTPγS Binding-type Detecting Method

In the GTPγS binding-type detecting method of the present invention, it may be detected whether or not a test compound is an antagonist or agonist against the platelet ADP receptor P2T$_{AC}$ by a GTPγS binding method (Lazareno, S. and Birdsall, N. J. M., Br. J. Pharmacol., 109, 1120-1127, 1993), by using the polypeptide for a detecting tool, a cell membrane fraction comprising the polypeptide, or a transformant expressing the polypeptide, for example, in accordance with the following procedure.

A cell membrane expressing the polypeptide for a detecting tool is mixed with $^{35}$S-labeled GTPγS (400 pmol/L) in a mixed solution of 20 mmol/L HEPES (pH 7.4), 100 mmol/L NaCl, 10 mmol/L MgCl$_2$, and 50 mmol/L GDP. After incubating in the presence of a test compound, and in the absence of the test compound, each reaction liquid is filtered by using a glass filter or the like, and then the radioactivity of remaining GTPγS on the filter is measured by using a liquid scintillation counter or the like. It may be detected whether or not the test compound is an agonist against the ADP receptor P2T$_{AC}$ by using the specific increase of the GTPγS binding in the presence of the test compound as an indicator. Further, it may be detected whether or not the test compound is an antagonist against the ADP receptor P2T$_{AC}$ by using the suppression in the increase of the GTPγS binding by a platelet ADP receptor P2T$_{AC}$ ligand (such as 2MeSADP or ADP) in the presence of the test compound, as an indicator.

(3) The Screening Method for an Antiplatelet Agent

A ligand, antagonist, or agonist against the platelet ADP receptor P2T$_{AC}$ may be screened by using the screening tool (including both the polypeptide-type screening tool for an antiplatelet agent and the transformant-type screening tool for an antiplatelet agent) of the present invention for an antiplatelet agent.

As previously described, ADP is known as an important factor which induces or promotes activation, adhesion, and aggregation of the platelet. Further, it is considered that ADP activates the platelet via a G protein-coupled ADP receptor P2T located in the platelet membrane (Biochem. J., 336, 513-523, 1998). Furthermore, it is considered that Ticlopidine or Clopidogrel, which is a known antiplatelet agent, functions by inhibiting the ADP receptor P2T$_{AC}$ via its metabolite in a body (Savi, P. J., Pharmaclo. Exp. Ther., 269, 772-777, 1994). It is shown that ARL67085 or derivatives thereof (ATP analogues), derivatives of Ap4A [P$^1$,P$^4$-di(adenosine-5')tetraphosphate], or the like exhibit an activity suppressing the platelet aggregation by ADP, by the P2T$_{AC}$ antagonist activity (Mills, D. C., Thromb. Hemost., 76, 835-856, 1996; Humphries, R. G., Trends Pharmacol. Sci., 16, 179-181, 1995; and Kim, B. K., Proc. Natl. Acad. Sci. USA, 89, 2370-2373, 1992). As shown in Example 7, ADP receptor P2T$_{AC}$ antagonists (such as 2MeSAMP or AR-C69931MX) exhibit the antiplatelet activity.

From the above information, the ligand or antagonist against the platelet ADP receptor P2T$_{AC}$ is useful as a substance capable of controlling the activation, adhesion, and aggregation of the platelet. Therefore, the above-mentioned polypeptide for a screening tool per se, or the transformant for a screening tool per se may be used for screening an antiplatelet agent. Namely, the polypeptide for a screening tool per se, or the transformant for a screening tool per se may be used for a screening tool.

Compounds to be tested which may be screened by using the screening tool of the present invention for an antiplatelet agent are not particularly limited, but there may be mentioned, for example, various known compounds (including peptides) registered in chemical files, compounds obtained by combinatorial chemistry techniques (Terrett, N. K. et al., Tetrahedron, 51, 8135-8137, 1995), or random peptides prepared by employing a phage display method (Felici, F. et al., J. Mol. Biol., 222, 301-310, 1991) or the like. In addition, culture supernatants of microorganisms, natural components derived from plants or marine organisms, or animal tissue extracts may be used as the test compounds for screening. Further, compounds (including peptides) obtained by chemically or biologically modifying compounds (including peptides) selected by the screening tool of the present invention for an antiplatelet agent may be used.

The screening methods of the present invention may be mainly divided into the following four groups in accordance with the detecting methods to be used. By using any one of the detecting methods, or a combination thereof, a substance which is useful as an antiplatelet agent can be screened by detecting whether or not a test compound is a ligand, antagonist, or agonist against the ADP receptor P2T$_{AC}$, and then selecting an antagonist among test compounds. The screening methods of the present invention, i.e., 1) a method for screening a ligand against the platelet ADP receptor P2T$_{AC}$ (hereinafter referred to as ligand screening method);

2) a method for screening an antagonist or agonist against the platelet ADP receptor $P2T_{AC}$ by the use of changes of an intracellular $Ca^{2+}$ concentration in the transformant as an indicator (hereinafter referred to as $Ca^{2+}$-type screening method);

3) a method for screening an antagonist or agonist against the platelet ADP receptor $P2T_{AC}$ by the use of changes of an intracellular cAMP concentration in the transformant as an indicator (hereinafter referred to as cAMP-type screening method); and 4) a method for screening an antagonist or agonist against the platelet ADP receptor $P2T_{AC}$ by the use of a GTPγS binding method (hereinafter referred to as GTPγS binding-type screening method) will be explained in this order hereinafter.

1) The Ligand Screening Method

The ligand screening method of the present invention is not particularly limited, so long as it comprises the steps of:

detecting whether or not a test compound is an ADP receptor $P2T_{AC}$ ligand by using the ligand detecting method of the present invention, and selecting the ADP receptor $P2T_{AC}$ ligand.

An ADP receptor $P2T_{AC}$ ligand can be screened by the use of the binding inhibition of the radioactive ligand obtained by the ligand detecting method as an indicator. For example, a test compound is reacted under the conditions described in Example 6 for a predetermined time, and then a test compound in which $IC_{50}$ is 10 µM or less (preferably 1 µM or less) may be selected as a ligand by the use of the binding inhibition of [$^3$H]-2MeSADP as an indicator.

A substance useful as an antiplatelet agent may be screened by applying the ligand which was screened by the ligand screening method of the present invention to the following $Ca^{2+}$-type screening method, cAMP-type screening method, and/or GTPγS binding-type screening method, and then selecting an antagonist.

2) The $Ca^{2+}$-type Screening Method

The $Ca^{2+}$-type screening method of the present invention is not particularly limited, so long as it comprises the steps of:

detecting whether or not a test compound is an ADP receptor $P2T_{AC}$ antagonist or agonist by using the $Ca^{2+}$-type detecting method of the present invention, and selecting the ADP receptor $P2T_{AC}$ antagonist or agonist.

An agonist can be screened by the use of the increase of an intracellular $Ca^{2+}$ concentration by a test compound in the transformant for $Ca^{2+}$-type detection as an indicator in the $Ca^{2+}$-type detecting method.

An antagonist can be screened by an indicator in which the increase of an intracellular $Ca^{2+}$ concentration in the transformant for $Ca^{2+}$-type detection by a platelet ADP receptor $P2T_{AC}$ agonist (such as 2MeSADP or ADP) is inhibited or suppressed by a test compound in the $Ca^{2+}$-type detecting method.

For example, a test compound is reacted under the conditions described in Example 3 for a predetermined time, and then a test compound in which $IC_{50}$ is 10 µM or less (preferably 1 µM or less) may be selected as a substance exhibiting the antagonist activity by the use of inhibition of the increase in an intracellular $Ca^{2+}$ concentration by 2MeSADP or ADP as an indicator.

A substance useful as an antiplatelet agent may be screened by screening an antagonist by using the $Ca^{2+}$-type screening method of the present invention.

3) The cAMP-type Screening Method

The cAMP-type screening method of the present invention is not particularly limited, so long as it comprises the steps of:

detecting whether or not a test compound is an ADP receptor $P2T_{AC}$ antagonist or agonist by using the cAMP-type detecting method of the present invention, and selecting the ADP receptor $P2T_{AC}$ antagonist or agonist.

An agonist can be screened by the use of the decrease of an intracellular cAMP concentration by a test compound in the transformant for cAMP-type detection as an indicator in the cAMP-type detecting method.

An antagonist can be screened by an indicator in which the decrease of an intracellular cAMP concentration in the transformant for cAMP-type detection by a platelet ADP receptor $P2T_{AC}$ agonist (such as 2MeSADP or ADP) is inhibited or suppressed by a test compound in the cAMP-type detecting method.

For example, a test compound is reacted under the conditions described in Example 4 or 5 for a predetermined time, and then a test compound in which $IC_{50}$ is 10 µM or less (preferably 1 µM or less) may be selected as a substance exhibiting the antagonist activity by the use of inhibition of the decrease in an intracellular cAMP concentration by 2MeSADP or ADP as an indicator.

A substance useful as an antiplatelet agent may be screened by screening an antagonist by using the cAMP-type screening method of the present invention.

4) The GTPγS Binding-type Screening Method

The GTPγS binding-type screening method of the present invention is not particularly limited, so long as it comprises the steps of:

detecting whether or not a test compound is an ADP receptor $P2T_{Ac}$ antagonist or agonist by using the GTPγS binding-type detecting method of the present invention, and selecting the ADP receptor $P2T_{AC}$ antagonist or agonist.

An agonist can be screened by the use of the increase of the specific GTPγS binding by a test compound as an indicator in the GTPγS binding-type detecting method.

An antagonist can be screened by an indicator in which the increase of the GTPγS binding by a platelet ADP receptor $P2T_{AC}$ agonist (such as 2MeSADP or ADP) is suppressed by a test compound.

A substance useful as an antiplatelet agent may be screened by screening an antagonist by using the GTPγS binding-type screening method of the present invention.

(4) Manufacture of the Pharmaceutical Composition for Antiplatelet

The present invention includes an antiplatelet agent containing, as an active ingredient, an ADP receptor $P2T_{AC}$ antagonist (for example, compounds, peptides, antibodies, or antibody fragments) selected by the screening methods 2) to 4) or by a combination of the screening methods 1) or 4).

It may be confirmed whether the selected ADP receptor $P2T_{AC}$ antagonist exhibits the antiplatelet activity by detecting the inhibiting activity of human platelet aggregation, for example, by the method described in Example 7.

Further, the present invention includes a method for manufacturing a pharmaceutical composition for antiplatelet comprising the steps of:

detecting, in a quality control test of a pharmaceutical composition for antiplatelet, whether or not it is an ADP receptor $P2T_{AC}$ ligand, antagonist, or agonist by the ligand detecting method, $Ca^{2+}$-type detecting method, cAMP-type detecting method, and/or GTPγS binding-type detecting method, and preparing a medicament.

The preparation of the present invention containing the ADP receptor P2T$_{AC}$ antagonist (for example, compounds, peptides, antibodies, or antibody fragments) as an active ingredient may be prepared using carriers, fillers, and/or other additives generally used in the preparation of medicaments, in accordance with the active ingredient.

Examples of administration include oral administration by tablets, pills, capsules, granules, fine granules, powders, oral solutions and the like, and parenteral administration by injections (e.g., intravenous, intramuscular, or the like), suppositories, transdermal preparations, transmucosal absorption preparations and the like. Particularly, in the case of peptides which are digested in the stomach, a parenteral administration such as intravenous injection or the like, or preparation techniques in which the polypeptide is not digested, such as a preparation technique disclosed in the WO95/28963 pamphlet, is preferable.

In the solid composition for use in the oral administration, one or more active substances may be mixed with at least one inert diluent such as lactose, mannitol, glucose, microcrystalline cellulose, hydroxypropylcellulose, starch, polyvinyl pyrrolidone, or aluminum magnesium silicate. In the usual way, the composition may contain additives other than the inert diluent, such as a lubricant, a disintegrating agent, a stabilizing agent, or a solubilizing or solubilization assisting agent. If necessary, tablets or pills may be coated with a sugar coating or a film of a gastric or enteric substance.

The liquid composition for oral administration may include, for example, emulsions, solutions, suspensions, syrups, and elixirs, and may contain a generally used inert diluent such as purified water or ethyl alcohol. The composition may contain additives other than the inert diluent, such as moistening agents, suspending agents, sweeteners, flavors, or antiseptics.

The injections for parenteral administration may include aseptic aqueous or non-aqueous solutions, suspensions, and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohols (e.g., ethanol), polysorbate 80 and the like. Such a composition may further contain a moistening agent, an emulsifying agent, a dispersing agent, a stabilizing agent, a solubilizing or solubilization assisting agent, an antiseptic or the like. These compositions may be sterilized, for example, by filtration through a bacteria retaining filter, blending of a germicide, or irradiation. Alternatively, they may be used by first making them into sterile solid compositions and dissolving them in sterile water or other sterile solvents for injection use, prior to their use.

The dose is optionally decided by taking into consideration the strength of each active ingredient selected by the aforementioned screening method, or symptoms, age, sex, or the like of each patient to be administered.

For example, in the case of oral administration, the usual dosage for an adult (60 kg in weight) is about 0.1 to 100 mg, preferably 0.1 to 50 mg per day. In the case of parenteral administration, the usual dosage is about 0.01 to 50 mg, preferably 0.01 to 10 mg per day in the form of an injection.

EXAMPLES

The present invention now will be further illustrated by, but is by no means limited to, the following Examples. The procedures may be performed in accordance with the known methods (Maniatis, T., et al., "Molecular Cloning—A Laboratory Manual", Cold Spring Harbor Laboratory, NY, 1982, or the like), unless otherwise specified.

Example 1

Isolation of ADP Receptor P2T$_{AC}$ Gene HORK3

In the present example, a full-length cDNA of an ADP receptor P2T$_{AC}$ gene HORK3 (hereinafter briefly referred to as HORK3 gene) was obtained by the PCR method using a human brain cDNA (manufactured by Clontech) as a template in accordance with the following procedure.

More particularly, an oligonucleotide consisting of the nucleotide sequence of SEQ ID NO: 3 was used as a forward primer, and an oligonucleotide consisting of the nucleotide sequence of SEQ ID NO: 4 was used as a reverse primer. At each of the 5'-termini of the forward and reverse primers, a nucleotide sequence containing the XbaI recognition sequence is added. A PCR was carried out using Taq DNA Polymerase (Ex Taq DNA polymerase; manufactured by Takara-shuzo) in the presence of 5% dimethyl sulfoxide (DMSO). In the PCR, a cycle consisting of treatments at 94° C. for 20 seconds, 58° C. for 20 seconds, and 74° C. for 1.5 minutes was repeated 5 times, a cycle consisting of treatments at 94° C. for 20 seconds, 55° C. for 20 seconds, and 74° C. for 1.5 minutes was repeated 5 times, and a cycle consisting of treatments at 94° C. for 20 seconds, 50° C. for 20 seconds, and 74° C. for 1.5 minutes was repeated 25 times. As a result, a DNA fragment of approximately 1.0 kbp was amplified. The DNA fragment was digested with XbaI, and inserted into the XbaI site of a plasmid pEF-BOS-dhfr (Mizushima, S. and Nagata, S., Nucleic Acids Res., 18, 5322, 1990) to obtain a plasmid pEF-BOS-dhfr-HORK3.

The nucleotide sequence of the HORK3 gene in the plasmid pEF-BOS-dhfr-HORK3 was determined using a DNA sequencer (ABI377 DNA Sequencer; manufactured by Applied Biosystems) by a dideoxy terminator method. The nucleotide sequence of the HORK3 gene was that of SEQ ID NO: 1.

The nucleotide sequence of SEQ ID NO: 1 contains an open reading frame (ORF) consisting of 1029 bases. The amino acid sequence (342 amino acids) deduced from the ORF was that of SEQ ID NO: 2.

Example 2

Confirmation of Expression Distribution of HORK3 Gene in Hemocytes

Blood was collected from a healthy volunteer by using heparin, and was centrifuged at 400×g for 10 minutes. The upper layer was taken as platelet-rich plasma.

To the lower layer, ⅓ volume of 6% dextran/physiological saline was added, and then the whole was allowed to stand at room temperature for 1 hour. The supernatant was taken and centrifuged at 150×g for 5 minutes, and then the pellet was suspended in HBSS (Hanks' Balanced Solt Solution). The suspension was layered on an equal volume of Ficoll (Ficoll Paque; Pharmacia), and then the whole was centrifuged at 400×g for 30 minutes. The resulting intermediate layer and pellet were taken as "a mononuclear cell fraction" and polymorphonuclear leukocytes, respectively.

CD16 microbeads (manufactured by Daiichi Pure Chemicals) were added to the polymorphonuclear leukocytes, and then "a neutrophil fraction" was separated from "an eosinophil fraction" by using a magnetic stand.

EDTA was added to the previously obtained platelet-rich plasma to a final concentration of 2 mmol/L, and then the whole was centrifuged at 2500×g for 15 minutes. The resulting pellet was resuspended in 120 mmol/L NaCl/2 mmol/L EDTA/30 mmol/L Tris-HCl (pH7.4), and then the suspension was centrifuged at 2500×g for 15 minutes to obtain the pellet as "a platelet fraction". The mononuclear cell fraction, neutrophil fraction, and eosinophil fraction were respectively washed with physiological saline.

Total RNAs were purified from the mononuclear cell fraction, neutrophil fraction, eosinophil fraction, and platelet fraction by using a commercially available total RNA purifying reagent (isogen; manufactured by Nippon Gene), respectively. The total RNA (5 μg) derived from each fraction was reacted with DNase (manufactured by Nippon Gene) at 37° C. for 15 minutes. The DNase-treated total RNA was converted to cDNA by a Superscript first-strand system (for RT-PCR; manufactured by GIBCO).

An analysis of an expression level of HORK3 mRNA in hemocytes was carried out by using each of the above cDNAs as a template and a sequence detector (Prism7700 Sequence Detector; manufactured by Applied Biosystems). An oligonucleotide consisting of the base sequence of SEQ ID NO: 5 and an oligonucleotide consisting of the base sequence of SEQ ID NO: 6 were used as a primer set. An oligonucleotide consisting of the nucleotide sequence of SEQ ID NO: 7, in which the 5'-terminus thereof was labeled with a fluorescence indicator FAM (6-carboxy-fluorescein) and the 3'-terminus thereof was labeled with a fluorescence indicator TAMRA (6-carboxy-tetramethyl-rhodamine), was used as a probe which specifically recognizes the HORK3 cDNA.

The PCR was carried out by using an commercially available PCR reagent (TaqMan PCR core reagent; manufactured by Applied Biosystems) and repeating a cycle consisting of treatments at 95° C. for 15 seconds and 60° C. for 60 seconds 50 times in the presence of 5% DMSO. Further, to obtain a standard curve for calculating an expression level of mRNA, a PCR was carried out under the same conditions by using a human genomic DNA as a template and the above primer set and probe [J. Neurosci. Methods. 98, 9-20 (2000)].

Furthermore, to calculate, as an internal standard, an expression level of human β-actin, a PCR was carried out under the same conditions, by using the above each cDNA or human genomic DNA as a template, an oligonucleotide consisting of the base sequence of SEQ ID NO: 8 and an oligonucleotide consisting of the base sequence of SEQ ID NO: 9 as a primer set, and an oligonucleotide consisting of the nucleotide sequence of SEQ ID NO: 10, in which the 5'-terminus thereof was labeled with a fluorescence indicator FAM and the 3'-terminus thereof was labeled with a fluorescence indicator TAMRA, as a probe specifically recognizing β-actin.

Expression levels of β-actin mRNA in the mononuclear cell fraction, neutrophil fraction, eosinophil fraction, and platelet fraction were 15000 copies, 19000 copies, 25000 copies, and 33000 copies per 1 ng of total RNA, respectively. In contrast, it was found that HORK3 mRNA was specifically expressed in platelets, but little expressed in mononuclear cells, neutrophils, and eosinophils.

Example 3

Confirmation of Increase in Intracellular $Ca^{2+}$ Concentration by 2MeSADP or ADP in C6-15 Cell Co-expressing HORK3 Protein and Gqi When most purines such as ADP, 2MeSADP (2-methylthio-ADP), or the like are added to a cell, the increase in intracellular $Ca^{2+}$ via an endogenous cellular membrane receptor is observed. Therefore, to analyze whether or not a protein derived from a gene introduced exogenously reacts with ADP or 2MeSADP, it is preferable to express the protein by using a cell which does not react with ADP or 2MeSADP. It is known that C6-15, a rat glioma cell line, does not react with ADP or the like (Change, K. et al., J. Biol. Chem., 270, 26152-26158, 1995). In the present example, the C6-15 cell was used to express the HORK3 protein.

Further, the plasmid pEF-BOS-dhfr-HORK3 obtained in Example 1 was used as an expression plasmid to be used for expressing the HORK3 protein.

An expression vector for expressing the chimeric protein of Gq and Gi used in the present example was prepared in accordance with a method of Conklin, B. R. et al. (Nature, 363, 274-276, 1993) by cloning a gene (hereinafter referred to as Gqi gene), which had been constructed by substituting five amino acids (Glu-Tyr-Asn-Leu-Val; the amino acid sequence of SEQ ID NO: 12) at the C-terminus of Gq with five amino acids (Asp-Cys-Gly-Leu-Phe; the amino acid sequence of SEQ ID NO: 11) at the C-terminus of Gi, into the plasmid pEF-BOS. The constructed plasmid was named plasmid pEF-BOS-Gqi.

The C6-15 cells were seeded on a 96-well plate (96 well Black/clear bottom plate, collagen I coated; manufactured by BECTON DICKINSON) so that the concentration of cells became $2\times10^4$ cells/well. After culturing for 48 hours, a gene transfection was carried out by using a transfection reagent (LipofectAMINE 2000; manufactured by GIBCO BRL) and the combination of the plasmid pEF-BOS-dhfr-HORK3 (50 ng/well) and the plasmid pEF-BOS-Gqi (50 ng/well). As a control, a gene transfection was carried out by using the combination of the plasmid pEF-BOS-dhfr (i.e., an empty vector without the HORK3 gene) and the plasmid pEF-BOS-Gqi, instead of the combination of the plasmid pEF-BOS-dhfr-HORK3 and the plasmid pEF-BOS-Gqi.

After 24 hours from the gene transfection procedure, the medium was discarded, and then HBBS (Hanks' Balanced Salt Solution; 100 μL/well) containing 4 μmol/L Fluo-3, AM (manufactured by Molecular Probe), 0.004% pluronic acid (trademark=Pluronic F127, manufactured by Molecular Probe), 1% fetal bovine serum (FBS), 20 mmol/L HEPES, and 2.5 mmol/L probenecid was added. After incubating at 37° C. for 1 hour, cells were washed with HBBS (manufactured by GIBCO) containing 20 mmol/L HEPES and 2.5 mmol/L probenecid 4 times, and then HBBS (100 μL/well) containing 20 mmol/L HEPES and 2.5 mmol/L probenecid was added.

A time course of the change in the intracellular $Ca^{2+}$ concentration was measured by using FLIPR (manufactured by Molecular Device). More particularly, after 10 seconds from the beginning of measurement, 2MeSADP or ADP was added to wells to a final concentration of $3\times10^{-5}$ mol/L to $1\times10^{-12}$ mol/L. After the addition, each fluorescence intensity was measured at an interval of 1 second for 50 seconds, and then at an interval of 6 seconds for 4 minutes.

The increase of the intracellular $Ca^{2+}$ concentration dependent upon the concentration of 2MeSADP or ADP was observed in the cells to which the combination of the plasmid pEF-BOS-dhfr-HORK3 and the plasmid pEF-BOS-Gqi had been transfected. In contrast, the change of the intracellular $Ca^{2+}$ concentration by 2MeSADP or ADP was not observed in the cells to which the combination of the plasmid pEF-BOS-dhfr (empty vector) and the plasmid pEF-BOS-Gqi had been transfected.

The change of the intracellular $Ca^{2+}$ concentration by 2MeSADP or ADP in the cells to which the plasmid pEF-BOS-dhfr-HORK3 and the plasmid pEF-BOS-Gqi had been transfected was measured, each peak value in various concentrations of 2MeSADP or ADP was plotted, and then the dependency upon the concentration was analyzed by using a Logistic regression method. As a result, it was found that $EC_{50}$ of 2MeSADP was 5.4 nmol/L, and that $EC_{50}$ of ADP was 220 nmol/L. As described above, it was confirmed that the dose-dependent change of the intracellular $Ca^{2+}$ concentration was induced by reacting with 2MeSADP or ADP in the transformant for $Ca^{2+}$-type detection co-expressing the polypeptide for a detecting tool and Gqi.

As described above, it was found that the HORK3 protein, one of the polypeptides for detection, is a Gi-coupled receptor which reacts with ADP. Further, as apparent from the results in the present example, it has become feasible to screen an agonist or antagonist by measuring the change of the intracellular $Ca^{2+}$ concentration in the C6-15 cell co-expressing the HORK3 protein (one of the polypeptides for a detecting tool) and Gqi.

Example 4

Confirmation of Inhibition of cAMP Production by 2MeSADP or ADP in CHO Cell Expressing HORK3 Protein It was found from Example 3 that the ADP receptor was a Gi-coupled receptor, and thus it is expected that the ADP receptor has an activity of suppressing the adenylate cyclase activity. Therefore, when the cAMP-type screening method of the present invention is carried out, it is preferable to select a cell line not having an activity of suppressing the adenylate cyclase activity by ADP or 2MeSADP, as a host cell to be used for expressing the ADP receptor protein. It was found that the CHO cell was the most preferable by searching for a cell in which an amount of cAMP produced by a forskolin stimulus was not decreased by ADP or 2MeSADP in accordance with the following procedure, and thus the CHO cell was used as the cell to be used for expressing the ADP receptor protein. In this connection, a dihydrofolate reductase (DHFR; an essential enzyme for de novo synthesis of nucleic acids) defective cell line [CHO-dhfr(−) line] was used in the present example. The plasmid pEF-BOS-dhfr-HORK3 was used as an expression plasmid to be used for expressing the HORK3 protein.

The CHO-dhfr(−) line was seeded on each 10 cm-petri dish ($1\times10^6$ cells/dish) by using an αMEM (with nucleic acids) medium. After culturing for 1 day, a gene transfection was carried out by using a transfection reagent (LipofectAMINE 2000; manufactured by GIBCO BRL) and the plasmid pEF-BOS-dhfr-HORK3 (8 µg). As a control, a gene transfection was carried out by using the plasmid pEF-BOS-dhfr (i.e., an empty vector without the HORK3 gene), instead of the plasmid pEF-BOS-dhfr-HORK3.

After 24 hours from the gene transfection procedure, the transfected cells were taken and suspended in an αMEM (without nucleic acids) medium containing 100 nmol/L methotrexate (a competitive inhibitor of DHFR; manufactured by Wako Pure Chemical Industries). Each suspension was gradually diluted and reseeded on each 10 cm-petri dish. Colonies which appeared after 2 weeks were individually taken, and used as a CHO cell expressing the HORK3 protein or a control CHO cell transfected with the empty vector in the following experiment.

The CHO cells expressing the HORK3 protein or the CHO cells transfected with the empty vector were seeded on a 24-well plate ($1\times10^5$ cells/well). After culturing for 1 day, cells were treated with an αMEM (without nucleic acids) medium containing 1 mmol/L 3-isobutyl-1-methylxanthine (manufactured by Sigma) and 0.1% BSA for 10 minutes, and then the combination of 3 µmol/L forskolin (manufactured by Wako Pure Chemical Industries) and 2MeSADP (a final concentration=$1\times10^{-12}$ to $1\times10^{-7}$ mol/L), or the combination of 3 µmol/L forskolin and ADP (a final concentration=$1\times10^{-10}$ to $1\times10^{-5}$ mol/L) was added dropwise. After incubating at 37° C. for 30 minutes, the culture supernatant was discarded, and then cells were dissolved in a cell lysis reagent contained in a cAMP-EIA system (BIOTRAK; manufactured by Amersham).

The amount of cAMP produced in each cell under each condition was measured by using the cAMP-EIA system in accordance with a protocol attached thereto. When the amount of cAMP produced by stimulating with 3 µmol/L forskolin alone was regarded as 100%, a concentration-dependent curve for the amount of cAMP in the presence of 2MeSADP or ADP was drawn. From the concentration-dependent curve, the responsiveness of 2MeSADP and ADP against the HORK3 protein were $EC_{50}$=0.07 nmol/L and $EC_{50}$=35 nmol/L, respectively.

In contrast, no changes in the amount of cAMP produced by the forskolin stimulus were observed in the CHO cell transfected with the empty vector, even if 2MeSADP or ADP was added.

Example 5

Effects of Inhibitors and Confirmation of Inhibition of cAMP Production by 2MeSADP or ADP in C6-15 Cell Expressing HORK3 Protein It was found that the C6-15 cell was also the most preferable as a cell in which the amount of cAMP produced by the forskolin stimulus was not decreased by ADP or 2MeSADP, and thus the C6-15 cell was also used as the cell to be used for expressing the ADP receptor protein.

The plasmid pEF-BOS-dhfr-HORK3 was used as an expression vector to be used for expressing the HORK3 protein.

The C6-15 cells were seeded on each 10 cm-petri dish ($1\times10^6$ cells/dish) by using a DMEM medium. After culturing for 1 day, an gene transfection was carried out by using a transfection reagent (LipofectAMINE 2000; manufactured by GIBCO BRL), and the plasmids pEF-BOS-dhfr-HORK3 (8 µg) and pEF-BOS-neo (Nucleic Acid Res., 18, 5322, 1990; 0.8 µg).

After 24 hours from the gene transfection procedure, the transfected cells were taken and suspended in a DMEM medium containing 0.6 mg/mL G418 (manufactured by GIBCO BRL). Each suspension was gradually diluted and reseeded on each 10 cm-petri dish. Colonies which appeared after 2 weeks were individually taken, and used as a C6-15 cell expressing the HORK3 protein in the following experiment.

The C6-15 cells expressing the HORK3 protein were seeded on a 96-well plate ($1\times10^4$ cells/well). After culturing for 1 day, cells were treated with a DMEM medium containing 1 mmol/L 3-isobutyl-1-methylxanthine (manufactured by Sigma) and 0.1% BSA for 10 minutes, and then the combination of 1 µmol/L forskolin (manufactured by Wako Pure Chemical Industries) and 2MeSADP (a final concentration=$1\times10^{-12}$ to $1\times10^{-7}$ mol/L), or the combination of 1 µmol/L forskolin and ADP (a final concentration=$1\times10^{-10}$ to $1\times10^{-5}$ mol/L) was added dropwise. After incubating at 37°

C. for 30 minutes, the culture supernatant was discarded, and then cells were dissolved in PBS containing 0.2% Triton X-100.

The amount of cAMP produced in each cell under each condition was measured by using a cAMP HTRF kit (manufactured by CIS bio international) in accordance with a protocol attached thereto. When the amount of cAMP produced by stimulating with 1 μmol/L forskolin alone was regarded as 100%, a concentration-dependent curve for the amount of cAMP in the presence of 2MeSADP or ADP was drawn. From the concentration-dependent curve, the responsiveness of 2MeSADP and ADP against the HORK3 protein were $EC_{50}=0.08$ nmol/L and $EC_{50}=42$ nmol/L, respectively. The C6-15 cell expressing the HORK3 protein exhibited almost the same property as that of the CHO cell expressing the HORK3 protein described in Example 4.

Next, effects of compounds, which are known to suppress the platelet aggregation, on the suppression of the amount of cAMP produced by the forskolin stimulus in the C6-15 cell expressing the HORK3 protein by 2MeSADP were examined. As the compounds suppressing the platelet aggregation, 2MeSAMP (2-methylthio-adenosine monophosphate) (Thromb. Haemost., 81, 111-117, 1999) or AR-C69931MX (N6-[2-methylthioethyl]-2-[3,3,3-trifluoropropylthio]-5'-adenylic acid, monoanhydride with dichloromethylenebiphosphonic acid) (J. Med. Chem., 42, 213-220, 1999) was used. In the above measurement system, cells were treated with a solution [prepared by dissolving 2MeSAMP ($10^{-7}$ to $10^{-4}$ mol/L) or AR-C69931MX ($10^{-12}$ to $10^{-6}$ mol/L) in DMEM medium containing 1 mmol/L 3-isobutyl-1-methylxanthine (manufactured by Sigma) and 0.1% BSA] for 10 minutes, and then the combination of 1 μmol/L forskolin (manufactured by Wako Pure Chemical Industries) and 10 nmol/L 2MeSADP was added dropwise. After incubating at 37° C. for 30 minutes, the culture supernatant was discarded, and then cells were dissolved in PBS containing 0.2% Triton X-100. The amount of cAMP produced was measured by using the cAMP HTRF kit in accordance with a protocol attached thereto. When the amount of cAMP produced by stimulating with 1 μmol/L forskolin alone was regarded as 0%, and that by stimulating with the combination of 1 μmol/L forskolin and 10 nmol/L 2MeSADP was regarded as 100%, a concentration-dependent curve of each inhibitor was drawn. From the concentration-dependent curve, inhibitory effects of 2MeSAMP and AR-C69931MX on the suppression by 2MeSADP in the amount of cAMP produced by the forskolin stimulus were $IC_{50}=5$ μmol/L and $IC_{50}=2.4$ nmol/L, respectively.

Example 6

Binding Assay of 2MeSADP to C6-15 Cell Expressing HORK3 Protein

The C6-15 cells expressing the HORK3 protein prepared in Example 5 were taken and washed, and then suspended in 20 mmol/L Tris-HCl (pH7.4) containing 5 mmol/L EDTA and a protease inhibitor cocktail set (Complete™; manufactured by Boeringer Mannheim). The whole was homogenized by using a POLYTRON, and ultracentrifuged. The pellet was suspended in 50 mmol/L Tris-HCl (pH7.4) containing 1 mmol/L EDTA, 100 mmol/L NaCl, 0.1% BSA, and Complete™ to obtain a membrane fraction.

After [$^3$H]-2MeSADP (manufactured by Moravek Biochemical) was added to 20 μg of the membrane fraction as a final concentration of 0.25 to 50 nmol/L, and was incubated in 250 μL of 50 mmol/L Tris-HCl (pH7.4) containing 1 mmol/L EDTA, 100 mmol/L NaCl, 0.1% BSA, and Complete™ at room temperature for 1 hour, the whole was collected on a glass filter by using a cell harvester. A microscintillator was added to the glass filter, and then a total amount of binding to the membrane fraction was measured by using a liquid scintillation counter. Further, an amount of non-specific binding to the membrane fraction was measured by adding 2MeSADP (a final concentration=50 μmol/L) in the above assay. As a result, it was found that [$^3$H]-2MeSADP was specifically bound to the membrane fraction of the C6-15 cell expressing the HORK3 protein. As a result of the Scatchard analysis for the binding, the dissociation constant of the [$^3$H]-2MeSADP binding to the membrane fraction of the C6-15 cell expressing the HORK3 protein was Kd=0.27 nmol/L, and the maximum binding was Bmax=3.7 pmol/mg. In contrast, such a specific binding was not observed in the membrane fraction of the host cell C6-15 not expressing the HORK3 protein.

Next, an effect of 2MeSAMP or AR-C69931MX was examined by using the membrane fraction of the C6-15 cell expressing the HORK3 protein prepared in Example 6, and by using an activity of inhibiting the [$^3$H]-2MeSADP binding as an indicator. More particularly, after 2MeSAMP ($10^{-7}$ to $10^{-4}$ mol/L) or AR-C69931MX ($10^{-12}$ to $10^{-6}$ mol/L) and 1 nmol/L [$^3$H]-2MeSADP were added to 20 μg of the membrane fraction from the C6-15 cell expressing the HORK3 protein, and were incubated at room temperature for 2 hours, the whole was collected on a glass filter by using a cell harvester. A microscintillator was added to the glass filter, and then radioactivity was measured by using a liquid scintillation counter. Further, radioactivity was measured by not adding the compound and by adding 2MeSADP (a final concentration=10 μmol/L) in the above assay, as a total amount of binding and an amount of non-specific binding, respectively. From the concentration-dependent curve of each compound, the inhibitory effects of 2MeSAMP and AR-C69931MX on the binding of 2MeSADP to the HORK3 protein were $IC_{50}=4.9$ μmol/L and $IC_{50}=9.8$ nmol/L, respectively.

In addition to the results in Example 3, the amount of cAMP produced by the forskolin stimulus in the CHO and C6-15 cells expressing the HORK3 protein was suppressed by 2MeSADP or ADP in Examples 4 and 5, respectively. These results made it clearer that the ADP receptor was coupled to Gi. Further, from the results in Examples 4 and 5, it has become feasible to screen an agonist or antagonist by measuring the change of the intracellular cAMP concentration in the CHO or C6-15 cell expressing the HORK3 protein (one of the polypeptides for a screening tool). Furthermore, it is possible to screening a ligand by measuring the inhibition of 2MeSADP binding to the membrane fraction of the C6-15 cell expressing the HORK3 protein, in accordance with the method described in Example 6.

As described above, the HORK3 protein is a Gi-coupled receptor expressed in platelets, from the results in Examples 2 to 6, and thus it is considered that the HORK3 protein is an entity of the platelet ADP receptor $P2T_{AC}$ in which the existence thereof has been suggested.

Example 7

Confirmation of Activity of Inhibiting Human Platelet Aggregation

Blood was collected from a healthy person (adult, male) by using 1/10 volume of sodium citrate, and then platelet-rich plasma(PRP) was prepared in accordance with a method of De Marco et al. (J. Clin. Invest., 77, 1272-1277, 1986). The PRP was used after preparing it to 3×10⁸ cells/mL by using an automatic blood cell counter (MEK6258; Nihon Kohden Corporation). As an inducer of aggregation, ADP which is a product manufactured by MC Medical Corporation was used. Further, 2MeSAMP or AR-C69931MX was used, and physiological saline was used as a solvent to be used for dissolving the compounds. In this connection, it was confirmed in Example 5 that 2MeSAMP or AR-C69931MX exhibited an activity as a HORK3 protein antagonist.

The platelet aggregation was measured by using an aggregometer (MCM Hema Tracer 212; MC Medical Corpration). More particularly, PRP (80 μL) and a sample (2MeSAMP or AR-C69931MX) or the solvent (10 μL) were incubated at 37° C. for 1 minute, and then 10 μL of ADP (20 to 200 μmol/L) was added. Changes of a transmitted light were recorded for 10 minutes, and then an aggregation inhibition (%) was calculated from the maximum aggregation rate.

Figure 2:
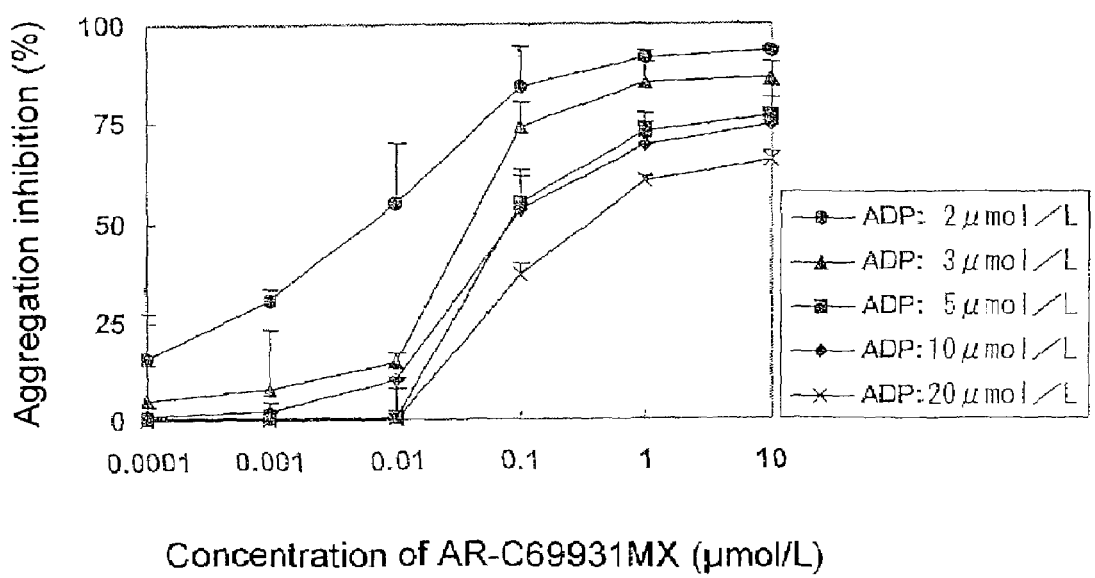
FIG. 2 is a graph showing the effect of AR-C69931MX in an ADP-induced platelet aggregation of PRP derived from human blood-treated with sodium citrate.

The results when 2MeSAMP and AR-C69931MX were used are shown in FIGS. 1 and 2, respectively. The data for 2MeSAMP (FIG. 1) are represented by the "average" of the experiment results obtained by using two volunteers. The data for AR-C69931MX (FIG. 2) are represented by the "average+ standard error" of the experiment results obtained by using three volunteers. Both agents inhibited the ADP-induced platelet aggregation concentration-dependently. The inhibitory strength was dependent on the concentration of ADP as an inducer.

It is apparent from the present example that an HORK3 protein antagonist exhibits an antiplatelet activity.

INDUSTRIAL APPLICABILITY

A substance inhibiting the platelet ADP receptor $P2T_{AC}$ activity exhibits an antiplatelet activity, and makes it possible to treat a thrombotic disorders.

Therefore, according to the screening tool of the present invention for an antiplatelet agent, it is possible to screen and evaluate a platelet ADP receptor $P2T_{AC}$ antagonist which is useful as an antiplatelet agent.

It is possible to select a platelet ADP receptor $P2T_{AC}$ antagonist and to screen a substance which is useful as an antiplatelet agent, by using the detecting method of the present method for an antagonist or agonist, or by using the combination of the ligand detecting method of the present invention and the detecting method of the present method for an antagonist or agonist.

Further, it is possible to manufacture a pharmaceutical composition for antiplatelet by preparing a medicament by using the substance selected by the above screening method as an active ingredient, and carriers, fillers, and/or other additives.

Furthermore, it is possible to use the detecting method of the present invention for a ligand, antagonist, or agonist not only for screening the substance useful as an antiplatelet agent, but also as a quality control test of a pharmaceutical composition for antiplatelet.

It is possible to manufacture a pharmaceutical composition for antiplatelet, by detecting whether or not a test compound is a platelet ADP receptor $P2T_{AC}$ ligand, antagonist, or agonist using the detecting method of the present invention for a ligand, antagonist, or agonist, and then by preparing a medicament using the antagonist or ligand.

Free Text in Sequence Listing

Features of "Artificial Sequence" are described in the numeric identifier <223> in the Sequence Listing. More particularly, each oligonucleotide consisting of the base sequence of SEQ ID NO: 3 or 4 is an artificially synthesized primer sequence.

As above, the present invention is explained with reference to particular embodiments, but modifications and improvements obvious to those skilled in the art are included in the scope of the present invention.

---

The invention claimed is:

1. A method of screening for an agent that inhibits platelet aggregation, comprising the steps of:

detecting whether or not a compound is an ADP receptor $P2T_{AC}$ ligand, antagonist, or agonist by at least one method selected from (a) a method for detecting whether or not the compound is an ADP receptor $p2T_{AC}$ ligand, comprising the steps of:

bringing a transformant cell membrane fraction comprising at least one of (1) a polypeptide comprising the amino acid sequence of SEQ ID NO: 2;

(2) a polypeptide comprising an amino acid sequence in which 1 to 10 amino acids are deleted, substituted, and/or added in the amino acid sequence of SEQ ID NO: 2, and exhibiting an activity of suppressing an adenylate cyclase activity by binding to ADP and coupling with Gi; or (3) a polypeptide comprising an amino acid sequence having a 95% or more homology with the amino acid sequence of SEQ ID NO: 2, and exhibiting an activity of suppressing an adenylate cyclase activity by binding to ADP and coupling with Gi, or bringing a transformant which is transformed with an expression vector comprising a DNA encoding at least one of said polypeptides (1) to (3), into contact with the compound, in the presence of a labeled ligand of an ADP receptor $P2T_{AC}$; and analyzing the amount of the labeled ligand which binds to the transformant cell membrane fraction or the transformant in the presence of and in the absence of the compound, wherein the ADP receptor $P2T_{AC}$ ligand is identified when the amount of labeled ligand that binds to the transformant cell membrane fraction or the transformant is lower in the presence of the compound than in the absence of the compound;

(b) a method for detecting whether or not the compound is an ADP receptor $P2T_{AC}$ antagonist or agonist, comprising the steps of:

bringing the compound and optionally a known ADP receptor $P2T_{AC}$ agonist into contact with a transformant which is transformed with an expression vector comprising a DNA encoding (1) a polypeptide comprising the amino acid sequence of SEQ ID NO: 2;

(2) a polypeptide comprising an amino acid sequence in which 1 to 10 amino acids are deleted, substituted, and/or added in the amino acid sequence of SEQ ID NO: 2, and exhibiting an activity of suppressing an adenylate cyclase activity by binding to ADP and coupling with Gi; or (3) a polypeptide comprising an amino acid sequence having a 95% or more homology with the amino acid sequence of SEQ ID NO: 2, and exhibiting an activity of suppressing an adenylate cyclase activity by binding to ADP and coupling with Gi said transformant co-expressing a G protein chimera comprising a polypeptide having an activity of promoting a phospholipase C activation, said G protein chimera having the amino acid sequence of SEQ ID NO: 11 at the C-terminus; and analyzing the intracellular $Ca^{2+}$ concentration in the transformant in the presence of and in the absence of the compound, wherein if the intracellular $Ca^{2+}$ increases in the presence of the compound and does not increase in the presence of the compound in a cell that does not express the polypeptide described in (1), (2) or (3), the compound is an ADP receptor $p2T_{AC}$ agonist and wherein if the intracellular $Ca^{2+}$ decreases in the presence of the compound and the known ADP receptor $p2T_{AC}$ agonist, the compound is an ADP receptor $p2T_{AC}$ antagonist; and (c) a method for detecting whether or not the compound is an ADP receptor $p2T_{AC}$ antagonist or agonist, comprising the steps of:

bringing a transformant which is transformed with an expression vector comprising a DNA encoding (1) a polypeptide comprising the amino acid sequence of SEQ ID NO: 2;

(2) a polypeptide comprising an amino acid sequence in which 1 to 10 amino acids are deleted, substituted, and/or added in the amino acid sequence of SEQ ID NO: 2, and exhibiting an activity of suppressing an adenylate cyclase activity by binding to ADP and coupling with Gi; or (3) a polypeptide comprising an amino acid sequence having a 95% or more homology with the amino acid sequence of SEQ ID NO: 2, and exhibiting an activity of suppressing an adenylate cyclase activity by binding to ADP and coupling with Gi into contact with the compound and optionally a known ADP receptor p2T$_{AC}$ agonist; and analyzing the intracellular cAMP concentration in the transformant in the presence of and in the absence of the compound, wherein if the intracellular cAMP decreases in the presence of the compound and does not decrease in the presence of the compound in a cell that does not express the polypeptide described in (1), (2) or (3), the compound is an ADP receptor P2T$_{AC}$ agonist and wherein if the intracellular cAMP does not decrease in the presence of the compound and the known ADP receptor p2T$_{AC}$ agonist, the compound is an ADP receptor p2T$_{AC}$ antagonist;

selecting the ADP receptor p2T$_{AC}$ antagonist as the agent; and confirming that the selected ADP receptor p2T$_{AC}$ antagonist exhibits a platelet aggregation inhibition activity by detecting inhibition of human platelet aggregation by the selected ADP receptor p2T$_{AC}$ antagonist.

2. A method of screening for an agent that inhibits platelet aggregation, comprising the steps of:

detecting whether or not a compound is an ADP receptor p2T$_{AC}$ ligand, antagonist, or agonist by at least one method selected from (a) a method for detecting whether or not the compound is an ADP receptor P2T$_{AC}$ ligand, comprising the steps of:

bringing a transformant cell membrane fraction comprising a polypeptide comprising the amino acid sequence of SEQ ID NO: 2, or a transformant which is transformed with an expression vector comprising a DNA encoding the polypeptide comprising the amino acid sequence of SEQ ID NO: 2, into contact with the compound, in the presence of a labeled ligand of an ADP receptor P2T$_{AC}$;and analyzing the amount of the labeled ligand which binds to the transformant cell membrane fraction or the transformant in the presence of and in the absence of the compound, wherein the ADP receptor p2T$_{AC}$ ligand is identified when the amount of labeled ligand that binds to the transformant cell membrane fraction or the transformant is lower in the presence of the compound than in the absence of the compound;

(b) a method for detecting whether or not the compound is an ADP receptor P2T$_{AC}$ antagonist or agonist, comprising the steps of:

bringing the compound and optionally a known ADP receptor P2T$_{AC}$ agonist into contact with a transformant which is transformed with an expression vector comprising a DNA encoding a polypeptide comprising the amino acid sequence of SEQ ID NO: 2, said transformant co-expressing a G protein chimera comprising a polypeptide having an activity of promoting a phospholipase C activation, said G protein chimera having the amino acid sequence of SEQ ID NO: 11 at the C-terminus; and analyzing the intracellular Ca$^{2+}$ concentration in the transformant in the presence of and in the absence of the compound, wherein if the intracellular Ca$^{2+}$ increases in the presence of the compound and does not increase in the presence of the compound in a cell that does not express the polypeptide comprising the amino acid sequence of SEQ ID NO: 2, the compound is an ADP receptor p2T$_{AC}$ agonist and wherein if the intracellular Ca$^{2+}$ decreases in the presence of the compound and the known ADP receptor P2T$_{AC}$ agonist, the compound is an ADP receptor p2T$_{AC}$ antagonist; and (c) a method for detecting whether or not the compound is an ADP receptor P2T$_{AC}$ antagonist or agonist, comprising the steps of:

bringing a transformant which is transformed with an expression vector comprising a DNA encoding a polypeptide comprising the amino acid sequence of SEQ ID NO: 2, into contact with the compound and optionally a known ADP receptor P2T$_{AC}$ agonist; and analyzing the intracellular cAMP concentration in the transformant in the presence of and in the absence of the compound, wherein if the intracellular cAMP decreases in the presence of the compound and does not decrease in the presence of the compound in a cell that does not express the polypeptide comprising the amino acid sequence of SEQ ID NO: 2, the compound is an ADP receptor p2T$_{AC}$ agonist and wherein if the intracellular cAMP does not decrease in the presence of the compound and the known ADP receptor P2T$_{AC}$ agonist, the compound is an ADP receptor p2T$_{AC}$ antagonist;

selecting the ADP receptor p2T$_{AC}$ antagonist as the agent; and confirming that the selected ADP receptor P2T$_{AC}$ antagonist exhibits a platelet aggregation inhibition activity by detecting inhibition of human platelet aggregation by the selected ADP receptor P2T$_{AC}$ antagonist.

* * * * *

UNITED STATES PATENT AND TRADEMARK OFFICE
CERTIFICATE OF CORRECTION

PATENT NO.      : 7,405,051 B2
APPLICATION NO. : 10/333844
DATED           : July 29, 2008
INVENTOR(S)     : Jun Takasaki et al.

It is certified that error appears in the above-identified patent and that said Letters Patent is hereby corrected as shown below:

On the title page, item (54), line 1 and col. 1, "SCREENING ANTIPLATELET" should read --SCREENING FOR ANTIPLATELET--.

In claim 1, column 33, line 25, "p2T$_{AC}$" should read --P2T$_{AC}$--.

In claim 1, column 33, line 48, "P2T$_{AC}$;and" should read --P2T$_{AC}$; and--.

In claim 1, column 34, line 43, "p2T$_{AC}$" should read --P2T$_{AC}$--.

In claim 1, column 34, line 45, "p2T$_{AC}$" should read --P2T$_{AC}$--.

In claim 1, column 34, line 46, "p2T$_{AC}$" should read --P2T$_{AC}$--.

In claim 1, column 34, line 48, "p2T$_{AC}$" should read --P2T$_{AC}$--.

In claim 1, column 35, line 2, "p2T$_{AC}$" should read --P2T$_{AC}$--.

In claim 1, column 35, line 13, "p2T$_{AC}$" should read --P2T$_{AC}$--.

In claim 1, column 35, line 14, "p2T$_{AC}$" should read --P2T$_{AC}$--.

In claim 1, column 35, line 15, "p2T$_{AC}$" should read --P2T$_{AC}$--.

In claim 1, column 35, line 17, "p2T$_{AC}$" should read --P2T$_{AC}$--.

In claim 1, column 35, line 20, "p2T$_{AC}$" should read --P2T$_{AC}$--.

In claim 2, column 35, line 24, "p2T$_{AC}$" should read --P2T$_{AC}$--.

In claim 2, column 35, line 36, "P2T$_{AC}$;and" should read --P2T$_{AC}$; and--.

In claim 2, column 35, line 41, "p2T$_{AC}$" should read --P2T$_{AC}$--.

In claim 2, column 36, line 16, "p2T$_{AC}$" should read --P2T$_{AC}$--.

In claim 2, column 36, line 20, "p2T$_{AC}$" should read --P2T$_{AC}$--.

In claim 2, column 36, line 21, "(c)a" should read --(c) a--.

In claim 2, column 36, line 38, "p2T$_{AC}$" should read --P2T$_{AC}$--.

UNITED STATES PATENT AND TRADEMARK OFFICE
CERTIFICATE OF CORRECTION

PATENT NO. : 7,405,051 B2
APPLICATION NO. : 10/333844
DATED : July 29, 2008
INVENTOR(S) : Jun Takasaki et al.

It is certified that error appears in the above-identified patent and that said Letters Patent is hereby corrected as shown below:

In claim 2, column 36, line 42, "p2$T_{AC}$" should read --P2$T_{AC}$--.

In claim 2, column 36, line 43, "p2$T_{AC}$" should read --P2$T_{AC}$--.

Signed and Sealed this

Seventh Day of October, 2008

JON W. DUDAS
*Director of the United States Patent and Trademark Office*

SEQUENCE LISTING

```
<160> NUMBER OF SEQ ID NOS: 12
<210> SEQ ID NO 1
<211> LENGTH: 1029
<212> TYPE: DNA
<213> ORGANISM: Homo sapiens
<220> FEATURE:
<221> NAME/KEY: CDS
<222> LOCATION: (1)..(1029)

<400> SEQUENCE: 1 atg caa gcc gtc gac aac ctc acc tct gcg cct ggg aac acc agt ctg      48
Met Gln Ala Val Asp Asn Leu Thr Ser Ala Pro Gly Asn Thr Ser Leu
 1               5                   10                  15 tgc acc aga gac tac aaa atc acc cag gtc ctc ttc cca ctg ctc tac      96
Cys Thr Arg Asp Tyr Lys Ile Thr Gln Val Leu Phe Pro Leu Leu Tyr
             20                  25                  30 act gtc ctg ttt ttt gtt gga ctt atc aca aat ggc ctg gcg atg agg     144
Thr Val Leu Phe Phe Val Gly Leu Ile Thr Asn Gly Leu Ala Met Arg
         35                  40                  45 att ttc ttt caa atc cgg agt aaa tca aac ttt att att ttt ctt aag     192
Ile Phe Phe Gln Ile Arg Ser Lys Ser Asn Phe Ile Ile Phe Leu Lys
     50                  55                  60 aac aca gtc att tct gat ctc ctc atg att ctg act ttt cca ttc aaa     240
Asn Thr Val Ile Ser Asp Leu Leu Met Ile Leu Thr Phe Pro Phe Lys
```

|     |     |     |     |     |     |     |     |     |     |     |     |      |
|-----|-----|-----|-----|-----|-----|-----|-----|-----|-----|-----|-----|------|
| 65  |     |     |     | 70  |     |     |     | 75  |     |     | 80  |      |
| att | ctt | agt | gat | gcc | aaa | ctg | gga | aca | gga | cca | ctg aga act ttt gtg | 288 |
| Ile | Leu | Ser | Asp | Ala | Lys | Leu | Gly | Thr | Gly | Pro | Leu Arg Thr Phe Val | |
|     |     |     |     | 85  |     |     |     | 90  |     |     | 95 | |
| tgt | caa | gtt | acc | tcc | gtc | ata | ttt | tat | ttc | aca | atg tat atc agt att | 336 |
| Cys | Gln | Val | Thr | Ser | Val | Ile | Phe | Tyr | Phe | Thr | Met Tyr Ile Ser Ile | |
|     |     |     | 100 |     |     |     |     | 105 |     |     | 110 | |
| tca | ttc | ctg | gga | ctg | ata | act | atc | gat | cgc | tac | cag aag acc acc agg | 384 |
| Ser | Phe | Leu | Gly | Leu | Ile | Thr | Ile | Asp | Arg | Tyr | Gln Lys Thr Thr Arg | |
|     |     |     | 115 |     |     |     |     | 120 |     |     | 125 | |
| cca | ttt | aaa | aca | tcc | aac | ccc | aaa | aat | ctc | ttg | ggg gct aag att ctc | 432 |
| Pro | Phe | Lys | Thr | Ser | Asn | Pro | Lys | Asn | Leu | Leu | Gly Ala Lys Ile Leu | |
|     | 130 |     |     |     |     | 135 |     |     |     |     | 140 | |
| tct | gtt | gtc | atc | tgg | gca | ttc | atg | ttc | tta | ctc | tct ttg cct aac atg | 480 |
| Ser | Val | Val | Ile | Trp | Ala | Phe | Met | Phe | Leu | Leu | Ser Leu Pro Asn Met | |
| 145 |     |     |     |     | 150 |     |     |     |     | 155 | 160 | |
| att | ctg | acc | aac | agg | cag | ccg | aga | gac | aag | aat | gtg aag aaa tgc tct | 528 |
| Ile | Leu | Thr | Asn | Arg | Gln | Pro | Arg | Asp | Lys | Asn | Val Lys Lys Cys Ser | |
|     |     |     |     | 165 |     |     |     |     | 170 |     | 175 | |
| ttc | ctt | aaa | tca | gag | ttc | ggt | cta | gtc | tgg | cat | gaa ata gta aat tac | 576 |
| Phe | Leu | Lys | Ser | Glu | Phe | Gly | Leu | Val | Trp | His | Glu Ile Val Asn Tyr | |
|     |     |     | 180 |     |     |     |     | 185 |     |     | 190 | |
| atc | tgt | caa | gtc | att | ttc | tgg | att | aat | ttc | tta | att gtt att gta tgt | 624 |
| Ile | Cys | Gln | Val | Ile | Phe | Trp | Ile | Asn | Phe | Leu | Ile Val Ile Val Cys | |
|     |     | 195 |     |     |     |     | 200 |     |     |     | 205 | |
| tat | aca | ctc | att | aca | aaa | gaa | ctg | tac | cgg | tca | tac gta aga acg agg | 672 |
| Tyr | Thr | Leu | Ile | Thr | Lys | Glu | Leu | Tyr | Arg | Ser | Tyr Val Arg Thr Arg | |
|     | 210 |     |     |     |     | 215 |     |     |     |     | 220 | |
| ggt | gta | ggt | aaa | gtc | ccc | agg | aaa | aag | gtg | aac | gtc aaa gtt ttc att | 720 |
| Gly | Val | Gly | Lys | Val | Pro | Arg | Lys | Lys | Val | Asn | Val Lys Val Phe Ile | |
| 225 |     |     |     |     | 230 |     |     |     |     | 235 | 240 | |
| atc | att | gct | gta | ttc | ttt | att | tgt | ttt | gtt | cct | ttc cat ttt gcc cga | 768 |
| Ile | Ile | Ala | Val | Phe | Phe | Ile | Cys | Phe | Val | Pro | Phe His Phe Ala Arg | |
|     |     |     |     | 245 |     |     |     |     | 250 |     | 255 | |
| att | cct | tac | acc | ctg | agc | caa | acc | cgg | gat | gtc | ttt gac tgc act gct | 816 |
| Ile | Pro | Tyr | Thr | Leu | Ser | Gln | Thr | Arg | Asp | Val | Phe Asp Cys Thr Ala | |
|     |     |     | 260 |     |     |     |     | 265 |     |     | 270 | |
| gaa | aat | act | ctg | ttc | tat | gtg | aaa | gag | agc | act | ctg tgg tta act tcc | 864 |
| Glu | Asn | Thr | Leu | Phe | Tyr | Val | Lys | Glu | Ser | Thr | Leu Trp Leu Thr Ser | |
|     |     | 275 |     |     |     |     | 280 |     |     |     | 285 | |
| tta | aat | gca | tgc | ctg | gat | ccg | ttc | atc | tat | ttt | ttc ctt tgc aag tcc | 912 |
| Leu | Asn | Ala | Cys | Leu | Asp | Pro | Phe | Ile | Tyr | Phe | Phe Leu Cys Lys Ser | |
|     | 290 |     |     |     |     | 295 |     |     |     |     | 300 | |
| ttc | aga | aat | tcc | ttg | ata | agt | atg | ctg | aag | tgc | ccc aat tct gca aca | 960 |
| Phe | Arg | Asn | Ser | Leu | Ile | Ser | Met | Leu | Lys | Cys | Pro Asn Ser Ala Thr | |
| 305 |     |     |     | 310 |     |     |     |     | 315 |     | 320 | |
| tct | ctg | tcc | cag | gac | aat | agg | aaa | aaa | gaa | cag | gat ggt ggt gac cca | 1008 |
| Ser | Leu | Ser | Gln | Asp | Asn | Arg | Lys | Lys | Glu | Gln | Asp Gly Gly Asp Pro | |
|     |     |     | 325 |     |     |     |     | 330 |     |     | 335 | |
| aat | gaa | gag | act | cca | atg | taa |     |     |     |     |     | 1029 |
| Asn | Glu | Glu | Thr | Pro | Met |     |     |     |     |     |     | |
|     |     |     | 340 |     |     |     |     |     |     |     |     | |

<210> SEQ ID NO 2
<211> LENGTH: 342
<212> TYPE: PRT
<213> ORGANISM: Homo sapiens

<400> SEQUENCE: 2

Met Gln Ala Val Asp Asn Leu Thr Ser Ala Pro Gly Asn Thr Ser Leu

```
            1               5              10              15
        Cys Thr Arg Asp Tyr Lys Ile Thr Gln Val Leu Phe Pro Leu Leu Tyr
                        20                  25                  30

Thr Val Leu Phe Phe Val Gly Leu Ile Thr Asn Gly Leu Ala Met Arg
                        35                  40                  45

Ile Phe Phe Gln Ile Arg Ser Lys Ser Asn Phe Ile Ile Phe Leu Lys
                        50                  55                  60

Asn Thr Val Ile Ser Asp Leu Leu Met Ile Leu Thr Phe Pro Phe Lys
         65                 70                  75                  80

Ile Leu Ser Asp Ala Lys Leu Gly Thr Gly Pro Leu Arg Thr Phe Val
                        85                  90                  95

Cys Gln Val Thr Ser Val Ile Phe Tyr Phe Thr Met Tyr Ile Ser Ile
                        100                 105                 110

Ser Phe Leu Gly Leu Ile Thr Ile Asp Arg Tyr Gln Lys Thr Thr Arg
                        115                 120                 125

Pro Phe Lys Thr Ser Asn Pro Lys Asn Leu Leu Gly Ala Lys Ile Leu
                        130                 135                 140

Ser Val Val Ile Trp Ala Phe Met Phe Leu Leu Ser Leu Pro Asn Met
        145                 150                 155                 160

Ile Leu Thr Asn Arg Gln Pro Arg Asp Lys Asn Val Lys Lys Cys Ser
                        165                 170                 175

Phe Leu Lys Ser Glu Phe Gly Leu Val Trp His Glu Ile Val Asn Tyr
                        180                 185                 190

Ile Cys Gln Val Ile Phe Trp Ile Asn Phe Leu Ile Val Ile Val Cys
                        195                 200                 205

Tyr Thr Leu Ile Thr Lys Glu Leu Tyr Arg Ser Tyr Val Arg Thr Arg
                        210                 215                 220

Gly Val Gly Lys Val Pro Arg Lys Val Asn Val Lys Val Phe Ile
        225                 230                 235                 240

Ile Ile Ala Val Phe Phe Ile Cys Phe Val Pro Phe His Phe Ala Arg
                        245                 250                 255

Ile Pro Tyr Thr Leu Ser Gln Thr Arg Asp Val Phe Asp Cys Thr Ala
                        260                 265                 270

Glu Asn Thr Leu Phe Tyr Val Lys Glu Ser Thr Leu Trp Leu Thr Ser
                        275                 280                 285

Leu Asn Ala Cys Leu Asp Pro Phe Ile Tyr Phe Phe Leu Cys Lys Ser
                        290                 295                 300

Phe Arg Asn Ser Leu Ile Ser Met Leu Lys Cys Pro Asn Ser Ala Thr
        305                 310                 315                 320

Ser Leu Ser Gln Asp Asn Arg Lys Lys Glu Gln Asp Gly Gly Asp Pro
                        325                 330                 335

Asn Glu Glu Thr Pro Met
                        340

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 3
cctctagaat gcaagccgtc gacaacctca cctc                              34
```

```
<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 4
cctctagact attacattgg agtctcttca tttg                              34

<210> SEQ ID NO 5
<211> LENGTH: 17
<212> TYPE: DNA
<213> ORGANISM: Homo sapiens

<400> SEQUENCE: 5
gcaagccgtc gacaacc                                                 17

<210> SEQ ID NO 6
<211> LENGTH: 24
<212> TYPE: DNA
<213> ORGANISM: Homo sapiens

<400> SEQUENCE: 6
tgattttgta gtctctggtg caca                                         24

<210> SEQ ID NO 7
<211> LENGTH: 24
<212> TYPE: DNA
<213> ORGANISM: Homo sapiens

<400> SEQUENCE: 7
cacctctgcg cctggtaaca ccag                                         24

<210> SEQ ID NO 8
<211> LENGTH: 17
<212> TYPE: DNA
<213> ORGANISM: Homo sapiens

<400> SEQUENCE: 8
cactgagcgc ggctaca                                                 17

<210> SEQ ID NO 9
<211> LENGTH: 22
<212> TYPE: DNA
<213> ORGANISM: Homo sapiens

<400> SEQUENCE: 9
cttaatgtca cgcacgattt cc                                           22

<210> SEQ ID NO 10
<211> LENGTH: 20
<212> TYPE: DNA
<213> ORGANISM: Homo sapiens

<400> SEQUENCE: 10
cttcaccacc acggccgagc                                              20

<210> SEQ ID NO 11
<211> LENGTH: 5
<212> TYPE: PRT
<213> ORGANISM: Homo sapiens

<400> SEQUENCE: 11
```

```
Asp Cys Gly Leu Phe
1               5

<210> SEQ ID NO 12
<211> LENGTH: 5
<212> TYPE: PRT
<213> ORGANISM: Homo sapiens

<400> SEQUENCE: 12

Glu Tyr Asn Leu Val
1               5
```